US009783482B2

(12) United States Patent
Slama Schwok et al.

(10) Patent No.: US 9,783,482 B2
(45) Date of Patent: Oct. 10, 2017

(54) ANTIVIRAL COMPOSITIONS DIRECTED AGAINST THE INFLUENZA VIRUS NUCLEOPROTEIN

(75) Inventors: Anny Slama Schwok, Saint Auban (FR); Bernard Delmas, Bourg-la-Reine (FR); Stephane Quideau, Talence (FR); Helene Bertrand, Paris (FR); Bogdan Tarus, Montigny les Metz (FR)

(73) Assignee: INSTITUT NATIONAL DE LA RECHERCHE AGRONOMIQUE, Paris (FR)

( * ) Notice: Subject to any disclaimer, the term of this patent is extended or adjusted under 35 U.S.C. 154(b) by 0 days.

(21) Appl. No.: 14/112,987

(22) PCT Filed: Apr. 20, 2012

(86) PCT No.: PCT/EP2012/001720
§ 371 (c)(1), (2), (4) Date: Dec. 11, 2013

(87) PCT Pub. No.: WO2012/143141
PCT Pub. Date: Oct. 26, 2012

(65) Prior Publication Data
US 2014/0163107 A1 Jun. 12, 2014

(51) Int. Cl.
*C07C 63/331* (2006.01)
*A61K 31/192* (2006.01)
(Continued)

(52) U.S. Cl.
CPC .......... *C07C 63/331* (2013.01); *A61K 31/192* (2013.01); *A61K 31/40* (2013.01);
(Continued)

(58) Field of Classification Search
CPC .. A61K 31/192; A61K 31/40; A61K 31/4196; A61K 31/5365; C07C 63/331;
(Continued)

(56) References Cited

U.S. PATENT DOCUMENTS 5,124,473 A 6/1992 Shroot et al.
6,333,435 B1 * 12/2001 Cai et al. ........................ 568/17
8,119,795 B2 2/2012 Eggenweiler et al.

FOREIGN PATENT DOCUMENTS

WO 2005030224 A1 4/2005
WO 2007134678 A2 11/2007
WO 2010143207 A1 12/2010

OTHER PUBLICATIONS

MeSH Descriptor Data, http://www.nlm.nih.gov/cgi/mesh/2009/MB_cgi?mode=&term=Naproxen accessed Nov. 21, 2014, published 2009.*

(Continued)

*Primary Examiner* — Savitha Rao
*Assistant Examiner* — Angela Brown-Pettigrew
(74) *Attorney, Agent, or Firm* — Young & Thompson

(57) ABSTRACT

A pharmaceutical composition for treating viral infections by an influenza type A virus, includes a compound capable of acting as an inhibitor of the binding of the viral RNA to the nucleoprotein of influenza type A viruses, and capable of binding to the viral-RNA-binding domain on the nucleoprotein. A pharmaceutical composition for treating viral infections by an orthomyxovirus, includes a compound capable of acting as an inhibitor of the binding of the viral RNA to the nucleoprotein of orthomyxoviruses, and capable of binding to the viral-RNA-binding domain on the nucleoprotein of the viruses. A compound acting as an inhibitor of the binding of the viral RNA to the nucleoprotein of influenza type A viruses, and binding to the viral-RNA-binding domain on the nucleoprotein of influenza type A viruses and a method for identifying such a compound having these properties are also described.

9 Claims, 12 Drawing Sheets

(51) Int. Cl.
  A61K 31/40    (2006.01)
  A61K 31/4196  (2006.01)
  A61K 31/5365  (2006.01)
  G01N 33/50    (2006.01)
  C07C 57/40    (2006.01)
(52) U.S. Cl.
  CPC ...... *A61K 31/4196* (2013.01); *A61K 31/5365* (2013.01); *C07C 57/40* (2013.01); *G01N 33/5008* (2013.01); *G01N 2333/11* (2013.01)
(58) Field of Classification Search
  CPC . C07C 57/40; G01N 33/5008; G01N 2333/11
  See application file for complete search history.

(56) References Cited

OTHER PUBLICATIONS

Abadi et al (Archiv der Pharmazie, Mar. 2001).*
Lejal et al., "Structure-Based Discovery of the Novel Antiviral Properties of Naproxen against the Nucleoprotein of Influenza A Virus", Antimicrobial Agents and Chemotherapy, 2013, vol. 57, No. 5, pp. 2231-2242.
Tarus et al., "Structure-Based design of novel naproxen derivatives targeting monomeric nucleoprotein of Influenza A virus", Journal of Biomolecular Structure and Dynamics, 2014, http://dx.doi.org/10.1080/07391102.2014.979230.
Fedichev et al., "Structure-based drug design of a new chemical class of small molecules active against influenza A nucleoprotein in vitro and in vivo", PLOS Currents Influenza, 2011, Edition 1, pp. 1-11, XP007921094.
Kao et al., "Identification of Influenza A nucleoprotein as an antiviral target", Nature Biotechnology, 2010, vol. 28, No. 6, pp. 600-607, XP55009857.
Gerritz et al., "Optimization and biophysical characterization of small molecules that inhibit influenza virus replication via binding to nucleoprotein (NP)", Abstracts of Papers American Chemical Society, 2011, vol. 241, p. 20-MEDI, XP009155908.
Siddiqui et al., "Thiosemicarbazone fragment embedded within 1,2,4-triazole ring as inhibitors of Entamoeba histolytica", Bioorganic & Medicinal Chemistry Letters, 2012, vol. 22, pp. 2768-2771, XP002684275.
Ye et al., "The mechanism by which influenza A virus nucleoprotein forms oligomers and binds RNA", Nature, 2006, vol. 444, pp. 1078-1082.
International Search Report, dated Oct. 15, 2012, from corresponding PCT application.
"ZINC19861005", Bioinformatics and Chemical Information Research Center, Nov. 12, 2008, XP002684273.

\* cited by examiner

A : infected    B: infected + 3mg naproxen    C: non-infected

```
                        SEQUENCE LISTING

<160> NUMBER OF SEQ ID NOS: 9

<210> SEQ ID NO 1
<211> LENGTH: 482
<212> TYPE: PRT
<213> ORGANISM: Influenza A virus (A/Wilson-Smith/1933(H1N1))

<400> SEQUENCE: 1

Arg Ser Tyr Glu Gln Met Glu Thr Asp Gly Glu Arg Gln Asn Ala Thr
1               5                   10                  15

Glu Ile Arg Ala Ser Val Gly Lys Met Ile Gly Gly Ile Gly Arg Phe
            20                  25                  30

Tyr Ile Gln Met Cys Thr Glu Leu Lys Leu Ser Asp Tyr Glu Gly Arg
        35                  40                  45

Leu Ile Gln Asn Ser Leu Thr Ile Glu Arg Met Val Leu Ser Ala Phe
    50                  55                  60

Asp Glu Arg Arg Asn Lys Tyr Leu Glu Glu His Pro Ser Ala Gly Lys
65                  70                  75                  80

Asp Pro Lys Lys Thr Gly Gly Pro Ile Tyr Arg Arg Val Asp Gly Lys
                85                  90                  95

Trp Met Arg Glu Leu Ile Leu Tyr Asp Lys Glu Glu Ile Arg Arg Ile
            100                 105                 110

Trp Arg Gln Ala Asn Asn Gly Asp Asp Ala Thr Ala Gly Leu Thr His
        115                 120                 125

Met Met Ile Trp His Ser Asn Leu Asn Asp Ala Thr Tyr Gln Arg Thr
    130                 135                 140

Arg Ala Leu Val Arg Thr Gly Met Asp Pro Arg Met Cys Ser Leu Met
145                 150                 155                 160

Gln Gly Ser Thr Leu Pro Arg Arg Ser Gly Ala Ala Gly Ala Ala Val
                165                 170                 175

Lys Gly Val Gly Thr Met Val Met Glu Leu Ile Arg Met Ile Lys Arg
            180                 185                 190

Gly Ile Asn Asp Arg Asn Phe Trp Arg Gly Glu Asn Gly Arg Arg Thr
        195                 200                 205

Arg Ile Ala Tyr Glu Arg Met Cys Asn Ile Leu Lys Gly Lys Phe Gln
    210                 215                 220

Thr Ala Ala Gln Arg Ala Met Val Asp Gln Val Arg Glu Ser Arg Asn
225                 230                 235                 240

Pro Gly Asn Ala Glu Phe Glu Asp Leu Ile Phe Leu Ala Arg Ser Ala
                245                 250                 255

Leu Ile Leu Arg Gly Ser Val Ala His Lys Ser Cys Leu Pro Ala Cys
            260                 265                 270

Val Tyr Gly Pro Ala Val Ala Ser Gly Tyr Asp Phe Glu Arg Glu Gly
        275                 280                 285

Tyr Ser Leu Val Gly Ile Asp Pro Phe Arg Leu Leu Gln Asn Ser Gln
    290                 295                 300

Val Tyr Ser Leu Ile Arg Pro Asn Glu Asn Pro Ala His Lys Ser Gln
305                 310                 315                 320

Leu Val Trp Met Ala Cys His Ser Ala Ala Phe Glu Asp Leu Arg Val
                325                 330                 335

Ser Ser Phe Ile Arg Gly Thr Lys Val Val Pro Arg Gly Lys Leu Ser
```

```
                    340                 345                 350
Thr Arg Gly Val Gln Ile Ala Ser Asn Glu Asn Met Glu Thr Met Glu
                355                 360                 365
Ser Ser Thr Leu Glu Leu Arg Ser Arg Tyr Trp Ala Ile Arg Thr Arg
            370                 375                 380
Ser Gly Gly Asn Thr Asn Gln Gln Arg Ala Ser Ser Gly Gln Ile Ser
385                 390                 395                 400
Ile Gln Pro Thr Phe Ser Val Gln Arg Asn Leu Pro Phe Asp Arg Pro
                405                 410                 415
Thr Ile Met Ala Ala Phe Thr Gly Asn Thr Glu Gly Arg Thr Ser Asp
                420                 425                 430
Met Arg Thr Glu Ile Ile Arg Leu Met Glu Ser Ala Arg Pro Glu Asp
                435                 440                 445
Val Ser Phe Gln Gly Arg Gly Val Phe Glu Leu Ser Asp Glu Lys Ala
                450                 455                 460
Ala Ser Pro Ile Val Pro Ser Phe Asp Met Ser Asn Glu Gly Ser Tyr
465                 470                 475                 480
Phe Phe

<210> SEQ ID NO 2
<211> LENGTH: 498
<212> TYPE: PRT
<213> ORGANISM: Influenza A virus (A/WSN/1933(H1N1))

<400> SEQUENCE: 2

Met Ala Thr Lys Gly Thr Lys Arg Ser Tyr Glu Gln Met Glu Thr Asp
1               5                   10                  15
Gly Glu Arg Gln Asn Ala Thr Glu Ile Arg Ala Ser Val Gly Lys Met
                20                  25                  30
Ile Asp Gly Ile Gly Arg Phe Tyr Ile Gln Met Cys Thr Glu Leu Lys
            35                  40                  45
Leu Ser Asp Tyr Glu Gly Arg Leu Ile Gln Asn Ser Leu Thr Ile Glu
    50                  55                  60
Arg Met Val Leu Ser Ala Phe Asp Glu Arg Arg Asn Lys Tyr Leu Glu
65                  70                  75                  80
Glu His Pro Ser Ala Gly Lys Asp Pro Lys Lys Thr Gly Gly Pro Ile
                85                  90                  95
Tyr Arg Arg Val Asp Gly Lys Trp Arg Arg Glu Leu Ile Leu Tyr Asp
                100                 105                 110
Lys Glu Glu Ile Arg Arg Ile Trp Arg Gln Ala Asn Asn Gly Asp Asp
            115                 120                 125
Ala Thr Ala Gly Leu Thr His Met Met Ile Trp His Ser Asn Leu Asn
    130                 135                 140
Asp Ala Thr Tyr Gln Arg Thr Arg Ala Leu Val Arg Thr Gly Met Asp
145                 150                 155                 160
Pro Arg Met Cys Ser Leu Met Gln Gly Ser Thr Leu Pro Arg Arg Ser
                165                 170                 175
Gly Ala Ala Gly Ala Ala Val Lys Gly Val Gly Thr Met Val Met Glu
                180                 185                 190
Leu Ile Arg Met Ile Lys Arg Gly Ile Asn Asp Arg Asn Phe Trp Arg
            195                 200                 205
Gly Glu Asn Gly Arg Arg Thr Arg Ile Ala Tyr Glu Arg Met Cys Asn
    210                 215                 220
Ile Leu Lys Gly Lys Phe Gln Thr Ala Ala Gln Arg Thr Met Val Asp
```

```
                225                 230                 235                 240
Gln Val Arg Glu Ser Arg Asn Pro Gly Asn Ala Glu Phe Glu Asp Leu
                    245                 250                 255
Ile Phe Leu Ala Arg Ser Ala Leu Ile Leu Arg Gly Ser Val Ala His
                    260                 265                 270
Lys Ser Cys Leu Pro Ala Cys Val Tyr Gly Ser Ala Val Ala Ser Gly
                    275                 280                 285
Tyr Asp Phe Glu Arg Glu Gly Tyr Ser Leu Val Gly Ile Asp Pro Phe
                    290                 295                 300
Arg Leu Leu Gln Asn Ser Gln Val Tyr Ser Leu Ile Arg Pro Asn Glu
305                 310                 315                 320
Asn Pro Ala His Lys Ser Gln Leu Val Trp Met Ala Cys His Ser Ala
                    325                 330                 335
Ala Phe Glu Asp Leu Arg Val Ser Ser Phe Ile Arg Gly Thr Lys Val
                    340                 345                 350
Val Pro Arg Gly Lys Leu Ser Thr Arg Gly Val Gln Ile Ala Ser Asn
                    355                 360                 365
Glu Asn Met Glu Thr Met Glu Ser Ser Thr Leu Glu Leu Arg Ser Arg
                    370                 375                 380
Tyr Trp Ala Ile Arg Thr Arg Ser Gly Gly Asn Thr Asn Gln Gln Arg
385                 390                 395                 400
Ala Ser Ser Gly Gln Ile Ser Ile Gln Pro Thr Phe Ser Val Gln Arg
                    405                 410                 415
Asn Leu Pro Phe Asp Arg Pro Thr Ile Met Ala Ala Phe Thr Gly Asn
                    420                 425                 430
Thr Glu Gly Arg Thr Ser Asp Met Arg Thr Glu Ile Ile Arg Leu Met
                    435                 440                 445
Glu Ser Ala Arg Pro Glu Asp Val Ser Phe Gln Gly Arg Gly Val Phe
                    450                 455                 460
Glu Leu Ser Asp Glu Lys Ala Thr Ser Pro Ile Val Pro Ser Phe Asp
465                 470                 475                 480
Met Ser Asn Glu Gly Ser Tyr Phe Phe Gly Asp Asn Ala Glu Glu Tyr
                    485                 490                 495
Asp Asn

<210> SEQ ID NO 3
<211> LENGTH: 498
<212> TYPE: PRT
<213> ORGANISM: Influenza A virus (A/Brevig Mission/1/1918(H1N1))

<400> SEQUENCE:

```
            100             105             110
Lys Glu Glu Ile Arg Arg Ile Trp Arg Gln Ala Asn Asn Gly Glu Asp
            115             120             125

Ala Thr Ala Gly Leu Thr His Met Met Ile Trp His Ser Asn Leu Asn
            130             135             140

Asp Ala Thr Tyr Gln Arg Thr Arg Ala Leu Val Arg Thr Gly Met Asp
145             150             155             160

Pro Arg Met Cys Ser Leu Met Gln Gly Ser Thr Leu Pro Arg Arg Ser
                165             170             175

Gly Ala Ala Gly Ala Ala Val Lys Gly Val Gly Thr Met Val Met Glu
                180             185             190

Leu Ile Arg Met Ile Lys Arg Gly Ile Asn Asp Arg Asn Phe Trp Arg
                195             200             205

Gly Glu Asn Gly Arg Arg Thr Arg Ile Ala Tyr Glu Arg Met Cys Asn
            210             215             220

Ile Leu Lys Gly Lys Phe Gln Thr Ala Ala Gln Arg Ala Met Met Asp
225             230             235             240

Gln Val Arg Glu Ser Arg Asn Pro Gly Asn Ala Glu Ile Glu Asp Leu
                245             250             255

Ile Phe Leu Ala Arg Ser Ala Leu Ile Leu Arg Gly Ser Val Ala His
                260             265             270

Lys Ser Cys Leu Pro Ala Cys Val Tyr Gly Pro Ala Val Ala Ser Gly
                275             280             285

Tyr Asp Phe Glu Arg Glu Gly Tyr Ser Leu Val Gly Ile Asp Pro Phe
            290             295             300

Arg Leu Leu Gln Asn Ser Gln Val Tyr Ser Leu Ile Arg Pro Asn Glu
305             310             315             320

Asn Pro Ala His Lys Ser Gln Leu Val Trp Met Ala Cys His Ser Ala
                325             330             335

Ala Phe Glu Asp Leu Arg Val Ser Ser Phe Ile Arg Gly Thr Arg Val
                340             345             350

Val Pro Arg Gly Lys Leu Ser Thr Arg Gly Val Gln Ile Ala Ser Asn
                355             360             365

Glu Asn Met Glu Thr Met Asp Ser Ser Thr Leu Glu Leu Arg Ser Arg
            370             375             380

Tyr Trp Ala Ile Arg Thr Arg Ser Gly Gly Asn Thr Asn Gln Gln Arg
385             390             395             400

Ala Ser Ala Gly Gln Ile Ser Val Gln Pro Thr Phe Ser Val Gln Arg
                405             410             415

Asn Leu Pro Phe Glu Arg Ala Thr Ile Met Ala Ala Phe Thr Gly Asn
                420             425             430

Thr Glu Gly Arg Thr Ser Asp Met Arg Thr Glu Ile Ile Arg Met Met
                435             440             445

Glu Ser Ala Arg Pro Glu Asp Val Ser Phe Gln Gly Arg Gly Val Phe
                450             455             460

Glu Leu Ser Asp Glu Lys Ala Thr Ser Pro Ile Val Pro Ser Phe Asp
465             470             475             480

Met Ser Asn Glu Gly Ser Tyr Phe Phe Gly Asp Asn Ala Glu Glu Tyr
                485             490             495

Asp Asn

<210> SEQ ID NO 4
<211> LENGTH: 498
```

<212> TYPE: PRT
<213> ORGANISM: Influenza A virus (A/Hong Kong/483/1997(H5N1))

<400> SEQUENCE: 4

```
Met Ala Ser Gln Gly Thr Lys Arg Ser Tyr Glu Gln Met Glu Thr Gly
1               5                   10                  15
Gly Glu Arg Gln Asn Ala Thr Glu Ile Arg Ala Ser Val Gly Arg Met
            20                  25                  30
Val Gly Gly Ile Gly Arg Phe Tyr Ile Gln Met Cys Thr Glu Leu Lys
        35                  40                  45
Leu Ser Asp Gln Glu Gly Arg Leu Ile Gln Asn Ser Ile Thr Ile Glu
    50                  55                  60
Arg Met Val Leu Ser Ala Phe Asp Glu Arg Arg Asn Arg Tyr Leu Glu
65                  70                  75                  80
Glu His Pro Ser Ala Gly Lys Asp Pro Lys Lys Thr Gly Gly Pro Ile
                85                  90                  95
Tyr Arg Arg Arg Asp Gly Lys Trp Val Arg Glu Leu Ile Leu Tyr Asp
            100                 105                 110
Lys Glu Glu Ile Arg Arg Ile Trp Arg Gln Ala Asn Asn Gly Glu Asp
        115                 120                 125
Ala Thr Ala Gly Leu Thr His Met Met Ile Trp His Ser Asn Leu Asn
    130                 135                 140
Asp Ala Thr Tyr Gln Arg Thr Arg Ala Leu Val Arg Thr Gly Met Asp
145                 150                 155                 160
Pro Arg Met Cys Ser Leu Met Gln Gly Ser Thr Leu Pro Arg Arg Ser
                165                 170                 175
Gly Ala Ala Gly Ala Ala Ile Lys Gly Val Gly Thr Met Val Met Glu
            180                 185                 190
Leu Ile Arg Met Ile Lys Arg Gly Ile Asn Asp Arg Asn Phe Trp Arg
        195                 200                 205
Gly Glu Asn Gly Arg Arg Thr Arg Ile Ala Tyr Glu Arg Met Cys Asn
    210                 215                 220
Ile Leu Lys Gly Lys Phe Gln Thr Ala Ala Gln Lys Ala Met Met Asp
225                 230                 235                 240
Gln Val Arg Glu Ser Arg Asn Pro Gly Asn Ala Glu Ile Glu Asp Leu
                245                 250                 255
Ile Phe Leu Ala Arg Ser Ala Leu Ile Leu Arg Gly Ser Val Ala His
            260                 265                 270
Lys Ser Cys Leu Pro Ala Cys Val Tyr Gly Leu Thr Val Ala Ser Gly
        275                 280                 285
Tyr Asp Phe Glu Arg Glu Gly Tyr Ser Leu Val Gly Ile Asp Pro Phe
    290                 295                 300
Arg Leu Leu Gln Asn Ser Gln Val Phe Ser Leu Ile Arg Pro Asn Glu
305                 310                 315                 320
Asn Pro Ala His Lys Ser Gln Leu Val Trp Met Ala Cys His Ser Ala
                325                 330                 335
Ala Phe Glu Asp Leu Arg Val Ser Ser Phe Ile Arg Gly Thr Arg Val
            340                 345                 350
Ile Pro Arg Gly Gln Leu Ser Thr Arg Gly Val Gln Ile Ala Ser Asn
        355                 360                 365
Glu Asn Val Glu Ala Met Asp Ser Ser Thr Leu Glu Leu Arg Ser Arg
    370                 375                 380
Tyr Trp Ala Ile Arg Thr Arg Ser Gly Gly Asn Thr Asn Gln Gln Arg
385                 390                 395                 400
```

```
Ala Ser Ala Gly Gln Ile Ser Val Gln Pro Thr Phe Ser Val Gln Arg
                405                 410                 415
Asn Leu Pro Phe Glu Arg Ala Thr Ile Met Ala Ala Phe Lys Gly Asn
            420                 425                 430
Thr Glu Gly Arg Thr Ser Asp Met Arg Thr Glu Ile Ile Arg Met Met
        435                 440                 445
Glu Ser Ala Arg Pro Glu Asp Val Ser Phe Gln Gly Arg Gly Val Phe
    450                 455                 460
Glu Leu Ser Asp Glu Lys Ala Thr Asn Pro Ile Val Pro Ser Phe Asp
465                 470                 475                 480
Met Ser Asn Glu Gly Ser Tyr Phe Phe Gly Asp Asn Ala Glu Glu Tyr
                485                 490                 495
Asp Asn

<210> SEQ ID NO 5
<211> LENGTH: 24
<212> TYPE: DNA
<213> ORGANISM: artificial sequence
<220> FEATURE:
<223> OTHER INFORMATION: ADN

<400> SEQUENCE: 5
tttgttacac acacacacgc tgtg                                          24

<210> SEQ ID NO 6
<211> LENGTH: 24
<212> TYPE: RNA
<213> ORGANISM: artificial sequence
<220> FEATURE:
<223> OTHER INFORMATION: ARN

<400> SEQUENCE: 6
uuuguuacac acacacacgc ugug                                          24

<210> SEQ ID NO 7
<211> LENGTH: 25
<212> TYPE: RNA
<213> ORGANISM: artificial sequence
<220> FEATURE:
<223> OTHER INFORMATION: ARN

<400> SEQUENCE: 7
uuuuuuuuuu uuuuuuuuuu uuuuu                                         25

<210> SEQ ID NO 8
<211> LENGTH: 24
<212> TYPE: DNA
<213> ORGANISM: artificial sequence
<220> FEATURE:
<223> OTHER INFORMATION: molecular beacon

<400> SEQUENCE: 8
atatatatcg acatagatat atat                                          24

<210> SEQ ID NO 9
<211> LENGTH: 24
<212> TYPE: RNA
```

```
<213> ORGANISM: artificial sequence
<220> FEATURE:
<223> OTHER INFORMATION: sequence tige boucle

<400> SEQUENCE: 9
auauauaucg acauagauau auau                                            24
```

ANTIVIRAL COMPOSITIONS DIRECTED AGAINST THE INFLUENZA VIRUS NUCLEOPROTEIN

The present patent application claims the priority of the French patent application FR11/01253 filed on 21 Apr. 2011 whose content is incorporated here by reference.

PRIOR ART

The present invention relates to pharmaceutical compositions comprising inhibiting compounds of the attachment of the viral RNA to the nucleoproteins of Influenza A viruses, the use of said compositions for the treatment of infection caused by a type-A Influenza virus as well as a method of identifying such inhibiting compounds.

The flu viruses, i.e. the Influenza viruses, are responsible every year for numerous infections of the respiratory pathways which kill between 250,000 and 500,000 people in the world. In addition to the seasonal strains, new strains have emerged over these last years: the Influenza A H1N1 virus which has emerged in pigs caused a relatively large pandemic in 2009 however causing low mortality. The Influenza A H5N1 strain, more commonly known as "avian influenza", once having emerged in avian animal races, proved particularly pathogenic, whereas the infection extended to humans with a mortality rate up to 60%.

The Influenza viruses responsible for the flu are single-stranded RNA viruses belonging to the Orthomyxoviridae family and forming the Influenza virus gender. This gender is broken down into three types of Influenza A, B or C viruses, whereas the type depends on the antigenic characteristics of certain proteins of said viruses and do not infect the same hosts.

The type-A Influenza viruses are able to infect different animal species, especially mammalians and birds, and exhibit a strong pathogenic power. They have the particularity of being subdivided into different subtypes depending on their hemagglutinin (HA) and neuraminidase (NA) surface proteins. To date, 16 hemagglutinins (H1 to H16) and 9 neuraminidases (N1 to N9) have been identified.

These viruses are structurally formed of 8 segments of negative polarity single-stranded RNA in a viral capsid itself protected by a phospholipid envelope. These 8 RNA segments provide encoding for the different viral proteins necessary to the transcription of negative-polarity RNA segments into positive-polarity RNA fragments but also necessary to viral replication, i.e. the nucleoproteins each to be associated with an RNA fragment as well as the PA, PB1 and PB2 proteins forming a ribonucleoprotein polymerase complex. The structural proteins of the virus such as the proteins of the envelope (neuraminidase and hemagglutinin) are also encoded by said proteins but the same goes for the M1 and M2 proteins situated below or in the viral envelope for maintaining the structure of the viruses as well as the non structural NS1 and NS2 proteins.

As the RNA fragments of the Influenza viruses have a negative polarity, they must be transcribed into messaging positive polarity RNA fragments by RNA-depending polymerase ANR viral enzymes in view of viral replication. The positive polarity RNA fragments then serve as messaging RNA necessary to protein translation.

The infection of host cells by Influenza A virus and the propagation of the virions produced by said cells is ensured by the activity of two proteins of the viral envelope: hemagglutinin and neuraminidase.

The HA hemagglutinin is a trimeric glycoprotein consisting of two subunits HA1 and HA2 with attachment sites specific to certain receptors for the attachment of the virus to the host cell and the release of the viral genome in the cytoplasm of said host cell. Hemagglutinin is indeed responsible for the attachment of the virus to the target cell at the sialic acid, also called N-acetyl-neuraminic acid, terminal of the glycoprotein or glycolipid chains of the membranar receptors of the host cell thus enabling the entry of the virus into the cell by endocytosis. Once the virus has merged with the membrane of the host cell, the viral genome contained in the capsid is released in the cytoplasm of the host cell.

The neuraminidase is also a surface protein of the Influenza A viruses. Although it is present in a smaller quantity than hemagglutinin, its role is still complementary. Indeed, neuraminidase has an enzymatic activity responsible for the cleavage of the osidic bonds formed between the hemagglutinin at the surface of the virions and the residues of sialic acid of the membrane of the host cell. The virions newly formed and attached to the membrane of the infected cell may hence be released, which prevents their aggregation at the host cell. This enzymatic activity also facilitates the detachment of the virions from the sialic acid-rich mucus and present in the respiratory epithelium.

In the face of the virulence of certain Influenza A virus strains, such as the H5N1 strain, but also against the great number of infections caused by the Influenza A viruses responsible for the seasonal flues causing a significant mortality rate, it proves increasingly necessary to develop inhibitors of these viruses for better protection and better treatment of the population.

The current treatments of the flu mostly consist of antiviral directed against the proteins of the Influenza A viruses.

Amantadine, distributed under the name of MANTADIX®, enables to inhibit replication of the virus by attachment to the M2 protein, ion channel protein of the capsid of the viruses. It also enables to inhibit the fusion between said capsid and the plasma membrane of the host cell as well as the release of the viral genetic material into the cytoplasm of the host cell.

Rimantadine also presents an action inhibiting the fusion of the viral capsid with the membrane of the host cell by inactivating the M2 protein.

Neuraminidase is also one of the existing antiviral targets with oseltamivir in particular (under the trade name of TAMIFLU®) and zanamivir (RELENZA®) inhibitors of said protein present at the surface of the viruses.

Other inhibitors of the Influenza viruses and directed against the RNA-dependent polymerase RNAs remain potentially usable but frequently interfere with the cellular functions of the host and are hardly specific to the Influenza viruses. Ribavirin is one of these inhibitors. On top of the treatment of Influenza viruses, it is also used for treating infections caused by the respiratory syncytial virus or the treatment of hepatitis C.

Unfortunately, the Influenza viruses develop more and more resistance to these antiviral treatments. These resistance phenomena are due to the high gene plasticity of the Influenza viruses. Two phenomena are implied in the emergence of a high variation of the virus genome: the antigenic drifts, caused by minor variations of the genome resulting from the substitution of one or several amino acids on one or two proteins (HA or NA), as well as the antigenic jumps, resulting from the mixed infection of two different type-A viruses whose fragments are recombined.

During the flu epidemic of 2008-2009, most of the H1N1 seasonal viruses circulating in the USA proved resistant to TAMIFLU® and all the isolated H3N2 strains were resistant to amantadines. It has also be noted that half of the individuals infected by the H5N1 virus are dead in spite of a treatment with both classes of antiviral directed against the surface proteins of the Influenza A viruses. It thus appears necessary to develop new inhibitors of the Influenza viruses as quickly as possible capable of treating the infections to said viruses while remaining less sensitive to the gene variation phenomena thereof.

SUMMARY OF THE INVENTION

In this optic, the inventors have identified new antivirals targeting the nucleoprotein (NP) of the Influenza A viruses, which protein associates with the viral RNA as well as a viral polymerase RNA to form the ribonucleoprotein complex responsible for the viral transcription and replication.

Constitutive of the structure of the viruses, the nucleoprotein of the type-A Influenza virus is an internal protein synthesised from the viral messaging RNA in the host cell, which confers it a mutation rate vastly smaller than that if the surface proteins subjected to the antigenic jumps and drifts as described previously. It has indeed been observed that the nucleoproteins of the type-H1 and H5 viruses have a very high identity rate (97%). Besides, the nucleoprotein is also advantageously not present in the host cells infected by viruses. Thus, any compound intended for acting specifically at the nucleoprotein will not provide a priori interference with the cellular mechanisms or the proteins of the host cell.

The inventors have hence identified compounds capable of binding specifically at the binding domain of the viral RNA on the nucleoprotein of the type-A Influenza viruses. The attachment of the viral RNA on the nucleoprotein of said viruses is not specific dependent on a particular sequence. It is the very structure of the protein which enables the viral RNA to be situated in a slot formed at the centre of the nucleoprotein to form the nucleoprotein complex to which the RNA polymerase will fix so as to form the ribonucleoprotein complex.

The inventors have indeed shown that the use of compounds capable of binding at said binding domain of the viral RNA to the nucleoprotein of the type-A Influenza virus prevents said RNA from attachment to the nucleoprotein, even competitively. The absence of attachment of the viral RNA to the nucleoprotein inhibits the formation of the of the ribonucleoprotein complex with the RNA polymerase, a complex necessary to the viral transcription and replication.

By analysing the structure of the binding domain of the viral RNA to the nucleoprotein of the Influenza viruses as well as the protein portions close to said domain, the inventors have also emphasised a correlation between the attachment of the RNA and the oligomerisation of the nucleoprotein; which implies that inhibitors capable of preventing the attachment of the viral RNA to the nucleoprotein of the type-A Influenza viruses will also cause a deficient at the oligomerisation of the nucleoprotein, a stage necessary to viral replication.

The use of compounds capable of binding at said binding domain of the viral RNA to the nucleoprotein hence enables to inhibit the viral replication at two levels, by inhibiting the formation of the ribonucleoprotein complex as well as by inhibiting the oligomerisation of the nucleoprotein.

The antivirals according to the invention are hence intended for treating subjects infected by an Influenza virus, notably type-A thanks to a specific action mechanism associated with the fixation site of the viral RNA to the nucleoprotein of said virus.

Besides, the antivirals current available to fight against the infections by certain strains of type-A Influenza viruses are governed by the variability constraints of said strains due to frequent mutations at the surface proteins of said viruses. The antivirals currently available are not only subjected to these mutation phenomena causing the development of antivirals capable of acting against the mutated viruses, their use is also limited to the specific treatment of infections by certain strains of type-A Influenza viruses, whereas said strains depend on the types of target proteins present at the surface of the viruses.

On the contrary, the antivirals according to the invention do not target the surface proteins of the Influenza viruses, notably type A, but are intended for attachment at the binding domain of the viral RNA to the nucleoprotein of said viruses.

The nucleoprotein of the Influenza viruses constitutes an internal protein which is not subject to the frequent mutation phenomena as observed in the surface proteins of these viruses. Thus, even the strains of Influenza viruses, notably type A, which will exhibit mutations especially at their surface proteins will remain targets of the antivirals according to the invention.

Besides, the nucleoprotein also forms a protein predominantly kept within the different strains of type-A Influenza virus and of other types. In addition to preserving the sequence of the nucleoprotein within the strains of Influenza viruses (above 90%), it has been demonstrated that the slot attachment the RNA in particular at said nucleoprotein does not vary at structural level between a H1N1 virus and a H5N1 virus (Ye et al, 2006, Ng et al, 2008). Thus, in addition to complying with the variability problems of nucleoprotein, the antivirals according to the invention advantageously cannot be used for treating a wide spectrum of infections by type-A Influenza virus, namely without any specific strain, contrary to the antivirals currently available.

The invention hence relates to new compounds having the property of acting as an inhibitor of the attachment of the viral RNA to the nucleoprotein of the type-A Influenza viruses by binding to the binding domain of the viral RNA to said nucleoprotein, thereby inhibiting the viral replication.

A first aspect of the invention hence concerns a pharmaceutical composition intended for the treatment of a viral infection by a type-A Influenza virus in a subject, which composition includes a compound having the property of acting as an inhibitor of the attachment of the viral RNA to the nucleoprotein of the type-A Influenza viruses, whereas said compound may bind to a site forming a site of at least 12 Ångströms (Å) in diameter centred on the TYR148 residue, belonging to the binding domain of the viral RNA on said nucleoprotein, said domain:

comprising the amino acids Arg65, Gln149, Tyr148, Arg150, Arg152, Arg156, Arg174, Arg175, Arg195, Arg199, Arg213, Arg214, Arg221, Arg236, Pro354, Arg355, Lys357, Arg361, Arg391, Lys184, Lys198, Gly212, Ile217, Ala218, Lys227, Lys229, Lys273 and Val353 of a sequence comprising the sequence SEQ ID No 1, preferably any amino acid situated at a distance less than 5 Ångströms of said amino acids, and being delineated by two loops, the first loop comprising the amino acid residues Glu73 to Lys90 and the second loop comprising the amino acid residues Gly200 to Arg214 of a sequence comprising the sequence SEQ ID No 1, and characterised in that said compound is selected among:

a Naproxen compound of formula (A) or one of its derivatives of formula (B) with:

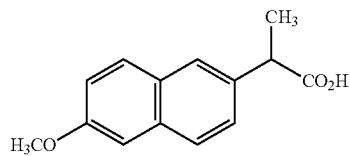

Formula (A)

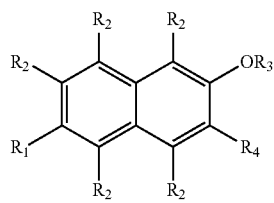

Formula (B)

With:

R1=-Ph(COOH)2 or -Ph(COOH)2-X—Ar with X=CH2 or O and Ar=Ph or PhOH or PhOMe or PhNH2 or imidazole or pyrrole Or R1=—CHR5R6 with:

R5=—(CH2)nCOOH or —(CH2)nSO3H with n=0-3 or —(CH2)nPhCOOH or -Ph(COOH)2 or —(CH2)nPhSO3H And R6=H, —CH3 or any linear aliphatic moiety or —(CH2)nOH with n=1-3 or CONH2 or Cl or F or R6=R5

R2=F, Cl or R2=R3

R3=H, CH3 or any linear aliphatic moiety or branched equivalents or —(CH2)nOH with n=0-4 or —(CH2)nNH2 with n=0-4 or —(CH2)nCONH2 with n=0-3

R4=OH or OR3 or H the triazole of formula (C) or one of its derivatives of formula (D) or (E) with:

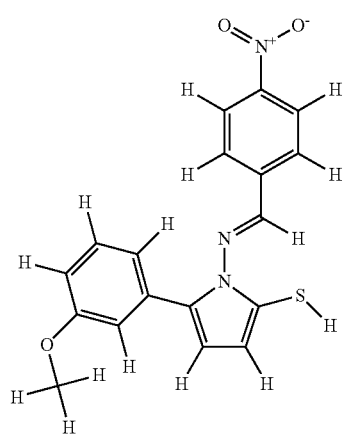

Formula (C)

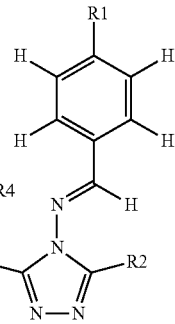

Formula (D)

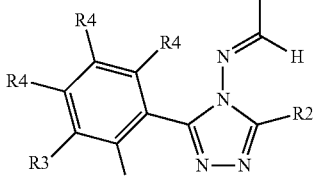

Formula (E)

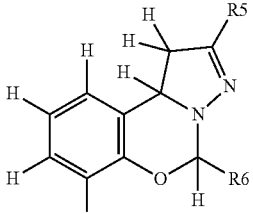

With:

R1=(CH2)n(COOH)m or (CH2)n(SO3H)m with n=0-3, m=1 or NO$_2$,

R2=H, F, Cl, or SH

R3=CH3 or any aliphatic moiety or —(CH2)n-OH n=0-4 or —(CH2)n-NH2 or OCH3 or O(CH2)nCH3 or O(CH2)nNH2

R4=H, F, Cl, with for the formula E:

R5=a carboxylate or sulfate or sulfonate phenyl -Ph(CH2)nCOOH or Ph(CH2)nSO3H or R5=H, F, Cl and R6=R5 or R6=-Ph-(OH)m (m=0-4) or -Ph-(OCH3) or R6=H, F, Cl, Preferably, said composition according to the invention is characterised in that said sequence comprising the sequence SEQ ID No 1 corresponds to the sequence SEQ ID No 2.

Preferably, said composition according to the invention is characterised in that said binding domain comprising more than 10% arginine amino acid residues, preferably more than 20% arginine amino acid residues.

Preferably, said composition according to the invention is characterised in that said compound is not a nitrated derivative of Naproxen as described in the international application PCT WO 2005/030224 A1 from line 1, page 2 to line 14, page 17.

Preferably, said composition according to the invention is characterised in that the subject is a mammalian, preferably a human, infected by a type-A Influenza virus.

According to another aspect, the invention relates to a pharmaceutical composition intended for the treatment of viral infection by an Orthomyxovirus in a subject, which composition comprises a compound as defined in claim 1.

Preferably, said composition according to the invention is characterised in that said compound is not a nitrated derivative of Naproxen as described in the international application PCT WO 2005/030224 A1 (NICOX) from line 1, page 2 to line 14, page 17.

Preferably, said composition according to the invention is characterised in that said compound is not a derivative of triazole as described in the international application PCT WO 2007134678 A2 (MERCK) from line 4, page 19 to line 20, page 39 and from line 19, page 45 to line 31, page 50.

Preferably, said composition according to the invention is characterised in that said compound is the Naproxen compound of formula (A) or one of its derivatives of formula (B) as defined in claim 1.

Preferably, said composition according to the invention is characterised in that said compound is a Naproxen compound of formula (L)

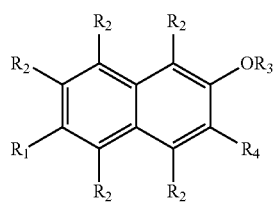

Formula (L)

With:

R1=-Ph(COOH)2 or -Ph(COOH)2-X—Ar with X=CH2 or O and Ar=Ph or PhOH or PhOMe or PhNH2 or imidazole or pyrrole Or R1=—CHR5R6 with:

R5=—(CH2)nCOOH or —(CH2)nSO3H with n=0-3 or —(CH2)nPhCOOH or -Ph(COOH)2 or —(CH2)nPhSO3H And R6=H, —CH3 or any linear aliphatic moiety or —(CH2)nOH with n=1-3 or CONH2 or Cl or F or R6=R5

R2=R3
R3=H

R4=H

Still more preferably, the composition according to the invention is characterised in that said compound is the Naproxen derivative compound of formula (L) or the Naproxen derivative compound of formula (G):

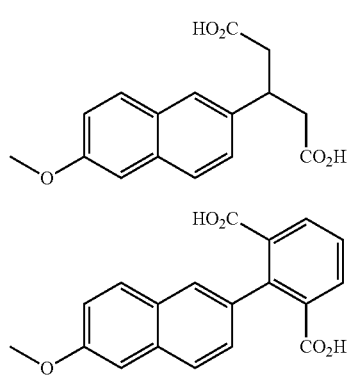

Formula (F)

Formula (G)

Preferably, said composition according to the invention is characterised in that said compound is a triazole of formula (C) or one of its derivatives of formulas (D) or (E) as defined previously.

Preferably, said composition according to the invention is characterised in that the subject is a mammalian, more preferably a human, infected by an Orthomyxovirus.

Preferably, said composition according to the invention is characterised in that said composition is intended for the treatment of a viral infection by an Influenza virus in a subject.

Preferably, said composition according to the invention is characterised in that the subject is a mammalian, preferably a human, infected by an Influenza virus.

Preferably, said composition according to the invention is characterised in that it may include a pharmaceutically acceptable support.

Another aspect of the invention relates to a compound having the property of acting as an inhibitor of the attachment of the viral NRA to the nucleoprotein of the type-A Influenza viruses, whereas said compound may bind to a site forming a sphere of at least 12 Ångströms (Å) in diameter centred on the TYR148 residue, belonging to the binding domain of the viral RNA on said nucleoprotein, said domain:

comprising the amino acids Arg65, Gln149, Tyr148, Arg150, Arg152, Arg156, Arg174, Arg175, Arg195, Arg199, Arg213, Arg214, Arg221, Arg236, Pro354, Arg355, Lys357, Arg361, Arg391, Lys184, Lys198, Gly212, Ile217, Ala218, Lys227, Lys229, Lys273 and Val353 of a sequence comprising the sequence SEQ ID No 1, preferably any amino acid situated at a distance less than 5 Ångströms of said amino acids, and being delineated by two loops, the first loop comprising the amino acid residues Glu73 to Lys90 and the second loop comprising the amino acid residues Gly200 to Arg214 of a sequence comprising the sequence SEQ ID No 1, and characterised in that said compound is selected among:

a Naproxen compound of formula (A) or one of its derivatives of formula (B) with:

Formula (A)

Formula (B)

With:

R1=-Ph(COOH)2 or -Ph(COOH)2-X—Ar with X=CH2 or 0 and Ar=Ph or PhOH or PhOMe or PhNH2 or imidazole or pyrrole Or R1=—CHR5R6 with:

R5=—(CH2)nCOOH or —(CH2)nSO3H with n=0-3 or —(CH2)nPhCOOH or -Ph(COOH)2 or —(CH2)nPhSO3H And R6=H, —CH3 or any linear aliphatic moiety or —(CH2)nOH with n=1-3 or CONH2 or Cl or F or R6=R5

R2=F, Cl or R2=R3

R3=H, —CH3 or any linear aliphatic moiety or branched equivalents or —(CH2)nOH with n=0-4 or —(CH2)nNH2 with n=0-4 or —(CH2)nCONH2 with n=0-3

R4=OH or OR3 or H the triazole of formula (C) or one of its derivatives of formula (D) or (E) with:

Formula (C)

[Chemical structure of Formula (C)]

Formula (D)

[Chemical structure of Formula (D)]

Formula (E)

[Chemical structure of Formula (E)]

With:
R1=(CH2)n(COOH)m or (CH2)n(SO3H)m with n=0-3, m=1 or $NO_2$,
R2=H, F, Cl, or SH
R3=CH3 or any aliphatic moiety or —(CH2)n-OH n=0-4 or —(CH2)n-NH2 or OCH3 or O(CH2)nCH3 or O(CH2)nNH2
R4=H, F, Cl,
with for the formula E:
R5=a carboxylate or sulfate or sulfonate phenyl -Ph(CH2)nCOOH or Ph(CH2)nSO3H or R5=H, F, Cl and
R6=R5 or R6=-Ph-(OH)m (m=0-4) or -Ph-(OCH3) or R6=H, F, Cl,
and characterised in that it is neither a derivative of triazole as described in the international application PCT WO 2007134678 A2 (MERCK) from line 4, page 19 to line 20, page 39 and from line 19, page 45 to line 31, page 50, nor a nitrated derivative of Naproxen as described in the international application PCT WO 2005/030224 A1 (NICOX) from line 1, page 2 to line 14, page 17.

Another aspect of the invention relates to a process for identifying a compound having the property of binding to the binding domain of the viral NRA to the nucleoprotein of the type-A Influenza viruses, said method comprising the following steps:

a) Modelling the (3D) three dimensional structure of the nucleoprotein of a type-A Influenza virus;

b) Generating a 3 dimension (3D) model of the binding domain of the viral RNA to said nucleoprotein from the structure obtained in a):

Said domain comprising the amino acids Arg65, Gln149, Tyr148, Arg150, Arg152, Arg156, Arg174, Arg175, Arg195, Arg199, Arg213, Arg214, Arg221, Arg236, Pro354, Arg355, Lys357, Arg361, Arg391, Lys184, Lys198, Gly212, Ile217, Ala218, Lys227, Lys229, Lys273 and Val353 of a sequence comprising the sequence SEQ ID No 1, preferably any amino acid situated at a distance less than 5 Ångströms of said amino acids, and Said domain being delineated by two loops, the first loop comprising the amino acid residues Glu 73 to Lys 90 and the second loop comprising the amino acid residues Gly 200 to Arg 214 of a sequence comprising the sequence SEQ ID No 1, c) Screening one or several compounds after the 3D model of the binding domain according to b) formed by a sphere of at least 12 Ångströms (Å) in diameter centred on the Tyr 148 residue;

d) Identifying a compound capable of binding at said binding domain of the viral RNA to the nucleoprotein, whereas said compound may inhibit the attachment of the NRA to the nucleoprotein of the type-A Influenza viruses and hence be used as a an inhibitor of viral replication.

Preferably, said method is characterised in that a sequence comprising the sequence SEQ ID No 1 is the sequence SEQ ID No 2.

Preferably, said method is characterised in that it comprises a complementary stage e) consisting in testing in vitro the capacity of a compound identified according to stage d) in inhibiting the attachment of the viral NRA to the nucleoprotein as well as viral replication.

Preferably, said method is characterised in that it includes a stage (f) consisting in selecting such a compound as being an inhibitor of viral replication.

DETAILED DESCRIPTION OF THE INVENTION

Figure 1:
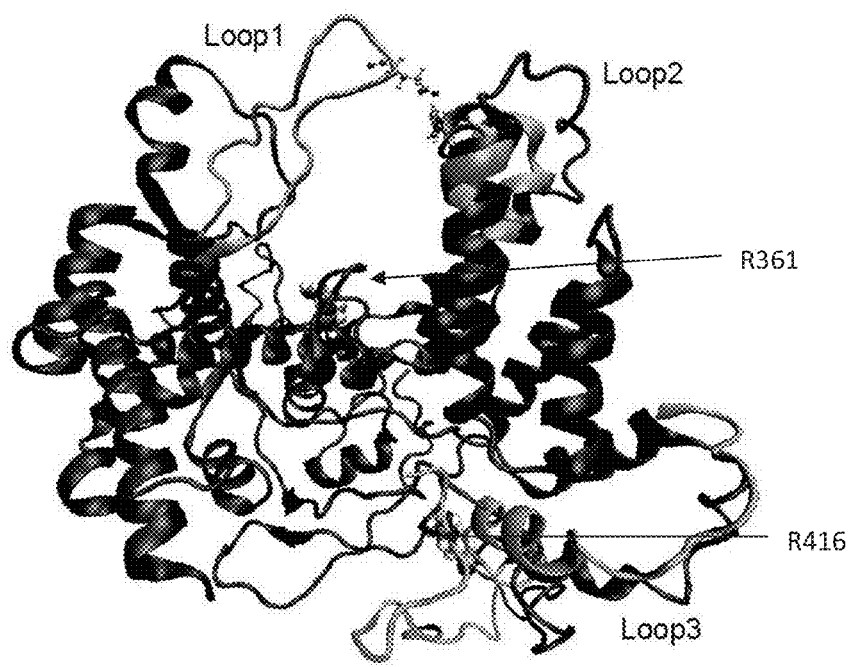
FIG. 1: Structure representative of the wild nucleoprotein of type-A Influenza virus.

According to a first aspect, the invention concerns a pharmaceutical composition intended for the treatment of a viral infection by a type-A Influenza virus in a subject, which composition includes a compound having the property of acting as an inhibitor of the attachment of the viral RNA to the nucleoprotein of the type-A Influenza viruses, whereas said compound may bind to a site forming a sphere of at least 12 Ångströms (Å) in diameter centred on the Tyr 148 residue, belonging to the binding domain of the viral RNA on said nucleoprotein, said domain:
  comprising the amino acids Arg65, Gln149, Tyr148, Arg150, Arg152, Arg156, Arg174, Arg175, Arg195, Arg199, Arg213, Arg214, Arg221, Arg236, Pro354, Arg355, Lys357, Arg361, Arg391, Lys184, Lys198, Gly212, Ile217, Ala218, Lys227, Lys229, Lys273 and Val353 of a sequence comprising the sequence SEQ ID No 1, preferably any amino acid situated at a distance less than 5 Ångströms of said amino acids, and
  being delineated by two loops, the first loop comprising the amino acid residues Glu73 to Lys90 and the second loop comprising the amino acid residues Gly200 to Arg214 of a sequence comprising the sequence SEQ ID No 1, By "nucleoprotein of the type-A Influenza virus" is meant the viral protein intended for associating with a viral nucleic fragment as well as a polymerase RNA in order to form the ribonucleoprotein complex responsible for the transcription as well as the viral replication. Nucleoproteins are proteins known to the man of the art and may exhibit variations according to the strains where they come from. Examples of protein sequences of nucleoproteins of type-A Influenza virus are as follows:
  SEQ ID No 2, nucleoprotein of the H1N1 strain of the type-A/WSN/1933 Influenza virus, GenBank accession number CY034135,
  SEQ ID No 3, nucleoprotein of the A/Brevig Mission/1/1918 (H1N1) strain, GenBank accession number AY744935,
  SEQ ID No 4, nucleoprotein of the A/HongKong/483/97 (H5N1) strain, GenBank accession number AF084277.

In a preferred manner, a sequence comprising the sequence SEQ ID No 1 is the sequence SEQ ID No 2.

A compound according to the invention is capable of binding to the nucleoprotein of the type-A Influenza viruses at the binding domain of the viral RNA thus preventing the latter from binding to the nucleoprotein. The inhibition of the attachment of the viral RNA on the nucleoprotein has two consequences which however remain correlated: on the one hand, the ribonucleoprotein complex, compound of the nucleoprotein, the viral RNA and the RNA polymerase, cannot form, on the other hand the inventors have demonstrated that the attachment of the viral RNA to the nucleoprotein played a part in the oligomerisation of the nucleoprotein, a stage necessary to the viral replication. Thus, the absence of attachment of the viral RNA to the nucleoprotein not only prevents the formation of the ribonucleoprotein complex but also the oligomerisation of the protein, which causes an absence of viral replication.

Due to the action mechanism of the compounds according to the invention at the binding domain of the viral RNA to the nucleoprotein of the type-A Influenza viruses, the pharmaceutical composition according to the invention enables to treat any subject infected by a type-A Influenza virus regardless of the strain and in the absence of problematics connected to the variability of nucleoprotein.

By "binding domain" with reference to the nucleoprotein of type-A Influenza virus is meant the protein domain to which the viral RNA fixes to form the nucleoprotein complex.

The binding site of the compounds is centred around a Tyrosine amino acid residue in position 148. This amino acid has been preserved in the nucleoproteins of the different types of type-A Influenza virus but also in the nucleoproteins of the type-B and C Influenza viruses and is directly involved in the formation of bonds between the viral RNA and the nucleoprotein.

Figure 2:
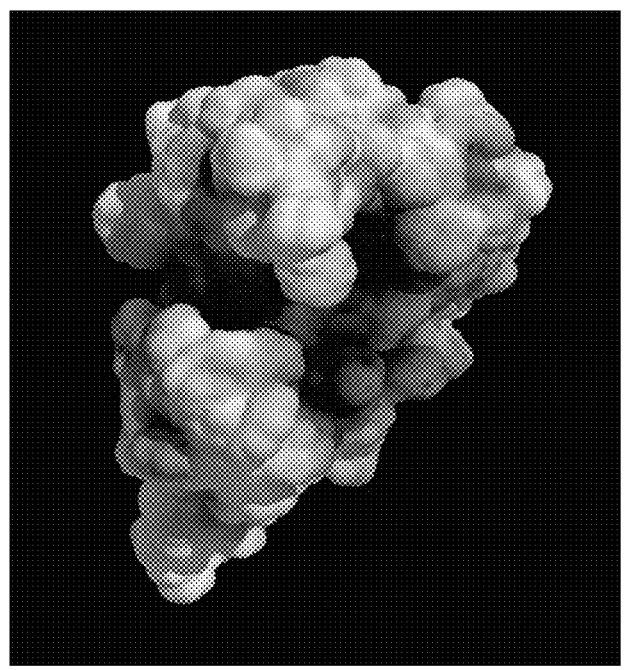
FIG. 2: Crystalline structure of the nucleoprotein of type-A Influenza virus showing a wide central slot for attachment the RNA.

The binding domain of the viral NRA to the nucleoprotein of the type-A Influenza viruses forms a distinct central slot in the structure of the nucleoprotein as can be observed in FIG. 2. Said domain constitutes an area rich in arginine and lysine basic amino acids promoting the binding with an inhibiting molecule or a nucleic acid.

In a preferred manner, said binding domain comprises more than 10% arginine amino acid residues, preferably more than 15% arginine amino acid residues.

Still more preferably, said binding domain comprises the following arginine amino acid residues: Arg65, Arg150, Arg152, Arg156, Arg174, Arg175, Arg195, Arg199, Arg213, Arg214, Arg221, Arg236, Arg355, Arg361, Arg391.

Still in a preferred manner, said binding domain comprises the following lysine amino acid residues: Lys357, Lys184, Lys198, Lys227, Lys229 and Lys273.

The inventors have also emphasised that the binding domain of the viral NRA to the nucleoprotein of the type-A Influenza viruses is delineated by several protein loops playing a part in the activity of the nucleoprotein. Thus, two loops have been identified as participating in the attachment of the viral RNA to the nucleoprotein: the first loop comprises the amino acid residues Glu73 to Lys90 and the second loop comprises the amino acid residues Gly200 to Arg214. These loops are visible on FIG. 1.

By "subject" is meant a mammalian, preferably a human, infected by a type-A Influenza virus.

In a preferred manner, a compound as defined previously is not a nitrated derivative of Naproxen as described in the international application PCT WO 2005/030224 A1 from line 1, page 2 to line 14, page 17, here incorporated by reference.

Naproxen is a non-steroidal anti-inflammatory drug (NSAID) of formula (A):

Formula (A)

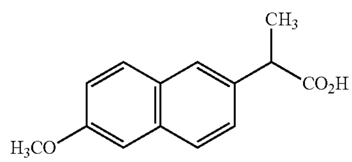

In a preferred manner, a compound as defined previously is a Naproxen compound of formula (A) or one of its derivatives of formula (B) with:

Formula (A)

Formula (B)

With:

R1=-Ph(COOH)2 or -Ph(COOH)2-X—Ar with X=CH2 or O and Ar=Ph or PhOH or PhOMe or PhNH2 or imidazole or pyrrole Or R1=—CHR5R6 with:

R5=—(CH2)nCOOH or —(CH2)nSO3H with n=0-3 or —(CH2)nPhCOOH or -Ph(COOH)2 or —(CH2)nPhSO3H And R6=H, —CH3 or any linear aliphatic moiety or —(CH2)nOH with n=1-3 or CONH2 or Cl or F or R6=R5

R2=F, Cl or R2=R3

R3=H, —CH3 or any linear aliphatic moiety or branched equivalents or —(CH2)nOH with n=0-4 or —(CH2)nNH2 with n=0-4 or —(CH2)nCONH2 with n=0-3

R4=OH or OR3 or H

According to another preferred embodiment, a compound as defined previously is a Naproxen compound of formula (A) or one of its derivatives of formula (B) with:

Formula (A)

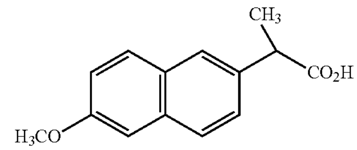

Formula (B)

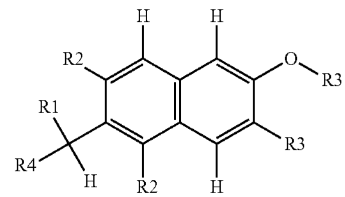

With:

R1=—(CH2)n(COOH)m or —(CH2)n(SO3H)m with n=0-3, m=1, carboxylate or sulfate or sulfonate phenyl -Ph(CH2)nCOOH or -Ph(COOH)2 or -Ph(CH2)n(SO3H)2

R2=H, F, Cl, or

R3=—CH3 or any aliphatic moiety CH3-(CH2)n- or —(CH2)n-OH with n=0-4 or —(CH2)n-NH2 or —(CH2)nCONH2

R3'=OH or OR3 or H

R4=—CH3 or any aliphatic moiety CH3-(CH2)n- or —(CH2)n-OH n=0-3 or CONH—R3 or H, F, Cl or R3=R2.

Still in a preferred manner, a compound as defined previously is a derivative of the Naproxen of formula (L):

Formula (L)

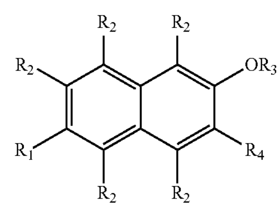

With:

R1=-Ph(COOH)2 or -Ph(COOH)2-X—Ar with X=CH2 or O and Ar=Ph or PhOH or PhOMe or PhNH2 or imidazole or pyrrole Or R1=—CHR5R6 with:

R5=—(CH2)nCOOH or —(CH2)nSO3H with n=0-3 or —(CH2)nPhCOOH or -Ph(COOH)2 or —(CH2)nPhSO3H And R6=H, —CH3 or any linear aliphatic moiety or —(CH2)nOH with n=1-3 or CONH2 or Cl or F or R6=R5

R2=R3

R3=H

R4=H

Still in a preferred manner, a compound as defined previously is a derivative of the Naproxen of formula (F) and designated hereafter "derivative of Naproxen A" or "Naproxen A":

Formula (F)

[Structure of Formula (F): 6-methoxynaphthalene with a substituent bearing two CO₂H groups]

Still more preferably, a compound as defined previously is a derivative of the Naproxen of formula (G) and designated hereafter "derivative of Naproxen c0" or "Naproxen c0":

Formula (G)

[Structure of Formula (G): 6-methoxynaphthalene linked to a benzene ring bearing two CO₂H groups]

Still in a preferred manner, a compound as defined previously is the triazole of formula (C) or one of its derivatives of formula (D) or (E) with:

Formula (C)

[Structure of Formula (C): nitrophenyl-imine-pyrrole with SH and methoxyphenyl substituents]

Formula (D)

[Structure of Formula (D): substituted phenyl-imine-triazole with R1, R2, R3, R4 substituents]

Formula (E)

[Structure of Formula (E): fused pyrazoline-chromene structure with R5 and R6 substituents]

With:

R1=(CH2)n(COOH)m or (CH2)n(SO3H)m with n=0-3, m=1, or NO2

R2=H, F, Cl, or SH

R3=CH3 or any aliphatic moiety or —(CH2)n-OH n=0-4 or —(CH2)n-NH2 or OCH3 or O(CH2)nCH3 or O(CH2)nNH2

R4=H, F, Cl, with for the formula E:

R5=a carboxylate or sulfate or sulfonate phenyl -Ph(CH2)nCOOH or

-Ph(CH2)nSO3H or R5=H, F, Cl and

R6=R5 or R6=-Ph-(OH)m (m=0-4) or -Ph-(OCH3) or R6=H, F, Cl,

Still in a preferred manner, a compound as defined previously is selected among a derivative of triazole of formula (H), (I), (J) or (K) respectively designated compound L410, compound 59, compound 72 and compound 88 with:

Formula (H)-L410

[Structure of Formula (H)-L410: nitrophenyl-imine-triazole with SH and methoxyphenyl substituents]

Formula (I)-59

[Structure of Formula (I)-59: dichlorophenyl-triazole with SH and imine-benzoic acid substituents]

Formula (J)-72

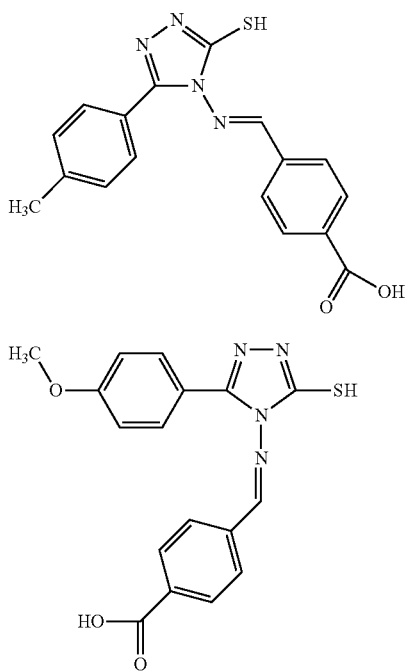

Formula (K)-88

According to a second aspect, the invention relates to a pharmaceutical composition intended for the treatment of a viral infection by an Orthomyxovirus in a subject, which composition includes a compound having the property of acting as an inhibitor of the attachment of the viral RNA to the nucleoprotein of the Orthomyxoviruses, said compound having the property of binding to the binding domain of the viral RNA to the nucleoprotein of said viruses as defined previously.

The Orthomyxovirus form the virus family of single-stranded RNA Orthomyxoviridae. This family includes in particular the five genders of type-A, type-B and type-C Influenza virus, the Isoviruses as well as the Thogotoviruses. The Influenza viruses are especially the cause for flu infections in vertebrates, said type-A viruses infecting humans as well as other mammalians and birds, the type-B Influenza viruses being responsible for the infection in humans and seals and the type-C Influenza viruses being responsible for the infection in humans and pigs. As regards the Isoviruses, they are responsible for salmon infections while the Thogotoviruses infect vertebrates as well as invertebrates such as fish parasites or mosquitoes.

By "subject" is meant a mammalian, preferably a human, infected by a virus belonging to the Orthomyvoviridae family.

In a preferred manner, a compound in a pharmaceutical composition intended for the treatment of viral infection by an Orthomyxovirus according to the invention is not a nitrated derivative of Naproxen as described in the application PCT WO 2005/030224 A1 (NICOX) from line 1, page 2 to line 14, page 17 here incorporated by reference.

Still in a preferred manner, a compound according to the invention in a pharmaceutical composition intended for the treatment of viral infection by an Orthomyxovirus is not a derivative of triazole as described in the international application PCT WO 2007134678 A2 (MERCK) from line 4, page 19 to line 20, page 39 and from line 19, page 45 to line 31, page 50 here incorporated by reference.

In a preferred manner, a compound according to the invention in a pharmaceutical composition intended for the treatment of viral infection by an Orthomyxovirus is the Naproxen compound of formula (A) or one of its derivatives of formula (B) as defined previously.

Still more preferably, a compound according to the invention in a pharmaceutical composition intended for the treatment of viral infection by an Orthomyxovirus is a derivative of Naproxen of formula (L).

Still more preferably, a compound according to the invention in a pharmaceutical composition intended for the treatment of viral infection by an Orthomyxovirus is a derivative of Naproxen of formula (F).

Still more preferably, a compound according to the invention in a pharmaceutical composition intended for the treatment of viral infection by an Orthomyxovirus is a derivative of Naproxen of formula (G).

Still in a preferred manner, a compound according to the invention in a pharmaceutical composition intended for the treatment of viral infection by an Orthomyxovirus is a triazole of formula (C) or one of its derivatives of formulas (D) or (E) as defined previously.

Still in a preferred manner, a compound according to the invention in a pharmaceutical composition intended for the treatment of viral infection by an Orthomyxovirus is a derivative of triazole selected among the compounds of formulae (H), (I), (J) and (K).

In a preferred manner, the pharmaceutical composition intended for the treatment of viral infection by an Orthomyxovirus is intended for the treatment of a viral infection by an Influenza virus in a subject.

Preferably, a subject according to the invention is a mammalian, more preferably a human, infected by an Influenza viruses.

A pharmaceutical composition according to the invention may also include a pharmaceutically acceptable support.

The term "pharmaceutically acceptable" refers to molecular entities or compositions which are physiologically tolerable and typically do not generate any allergic reaction or similar unbearable reaction, such as intestine disorder or vertigo, during administration into the subject. Preferably, the term "pharmaceutically acceptable" used here means approved by a regulatory agency of a federal government or of a state or listed in the American pharmacopoeia or any other generally recognised pharmacopoeia for use in animals and more particularly in humans.

The term "support" refers to a diluent, an adjuvant, an excipient or a vehicle with which the compound according to the invention is administered. Such pharmaceutical supports can be sterile liquids, such as water or oils, including those of petrol, animal, vegetable or still synthetic origin, such as peanut, soya, mineral or still sesame oils. Water or any aqueous solution, salt solution or still dextrose or glycerol aqueous solution are employed preferably as supports, and more particularly for injectable solutions. By way of example, the composition may comprise emulsions, microemulsions, oil in water emulsions, anhydrous lipids and water in oil emulsions, or other types of emulsions. Pharmaceutically acceptable supports are described in the book "Remington's Pharmaceutical Sciences" by E. W. Martin.

The composition according to the invention may further comprise one or several additives such as diluents, excipients, stabilisers and preservatives. Such additives are well known to the man of the art and are described especially in <<Ullmann's Encyclopedia of Industrial Chemistry, 6th Ed.>> (various publishers, 1989-1998, Marcel Dekker); and in "Pharmaceutical Dosage Forms and Drug Delivery System"s (ANSEL et al., 1994, WILLIAMS & WILKINS).

The composition according to the invention can be in a form which can be administered by parenteral route, notably by intravenous, intraperitoneal, intradermic, subcutaneous or still intraarterial route or in a form which can administered by oral route or by pulmonary or nasal route. The selection of the administration route of the composition according to the invention will depend on the form of the composition to be administered, on the pharmaceutically acceptable supports selected or still the efficiency speed required. The man of the art, based on his knowledge in the field, will be able to select the best suitable administration route.

In a preferred embodiment, said composition is intended for an administration by parenteral route.

According to another preferred embodiment, said composition is intended for an administration by oral route.

The dose of the inhibiting compound in the pharmaceutical composition according to the invention will be adjusted according to the administration type of the composition.

According to a third aspect, the invention relates to a compound having the property of acting as an inhibitor of the attachment of the viral RNA to the nucleoprotein of the type-A Influenza viruses, said compound having the property of binding to the binding domain of the viral RNA to the nucleoprotein of the type-A Influenza viruses as defined previously, and characterised in that it is neither a derivative of triazole as described in the international application PCT WO 2007134678 A2 (MERCK) from line 4, page 19 to line 20, page 39 and from line 19, page 45 to line 31, page 50 here incorporated by reference, nor a nitrated derivative of Naproxen as described in the application PCT WO 2005/030224 A1 (NICOX) from line 1, page 2 to line 14, page 17 here incorporated by reference.

In a preferred manner, a compound according to the invention is the Naproxen compound of formula (A) or one of its derivatives of formulas (B) as defined previously.

Still more preferably, a compound according to the invention is a Naproxen derivative of formula (L).

Still more preferably, a compound according to the invention is the Naproxen derivative of formula (F).

Still more preferably, a compound according to the invention is the Naproxen derivative of formula (G).

Still in a preferred manner, a compound according to the invention is a triazole of formula (C) or one of its derivatives of formulas (D) or (E) as defined previously.

Still in a preferred manner, a compound according to the invention is a derivative of triazole selected among the compounds of formulae (H), (I), (J) and (K).

According to a fourth aspect, the invention relates to a method of treating an infection by an Orthomyxovirus, preferably an Influenza virus or a type-A Influenza virus, in a subject, which method includes the administration of a therapeutically effective quantity of a composition as described previously into said subject.

As used for the present treatment method, the term "subject" corresponds to a mammalian, preferably said subject is a human, infected by an Orthomyxovirus, preferably an Influenza virus or a type-A Influenza virus.

The inventors have indeed demonstrated that the use of a compound capable of binding to the slot in which the viral RNA is situated at the nucleoprotein of the Influenza A viruses prevented the bonding of the viral RNA at said nucleoprotein. The inventors have also demonstrated that the absence of attachment of the viral RNA to the nucleoprotein led to the absence of oligomerisation of said protein.

Thus, the use of a compound according to the invention not only enables to inhibit the attachment of the viral RNA to the nucleoprotein but also to inhibit the oligomerisation of said protein, the consequence of both these inhibition being the inhibition of the viral replication.

By "therapeutically effective quantity" is meant a sufficient quantity to lead to the desired biological effect, in the present case a decrease of the viral titer resulting from an infection by a type-A Influenza virus.

The compound according to the invention can be administered in one or several goes, whereas the amount of said compound is then adjusted according to the number of administrations envisaged. Thus, the amount of compound to be administered for the treatment of an infection by a type-A Influenza virus according to the invention may range between 0.1 milligram (mg) and 2000 mg per day.

The man of the art will be in a position to determine said therapeutically effective quantity in the light of his general knowledge (see for example Berkow (1987), infra, Goodman (1990), infra, Avery (1987), infra, Ebadi, Pharmacology, Little, Brown and Co., Boston, Mass. (1985), and Katsung (1992), infra) and/or using simple routine experiments.

Figure 5:
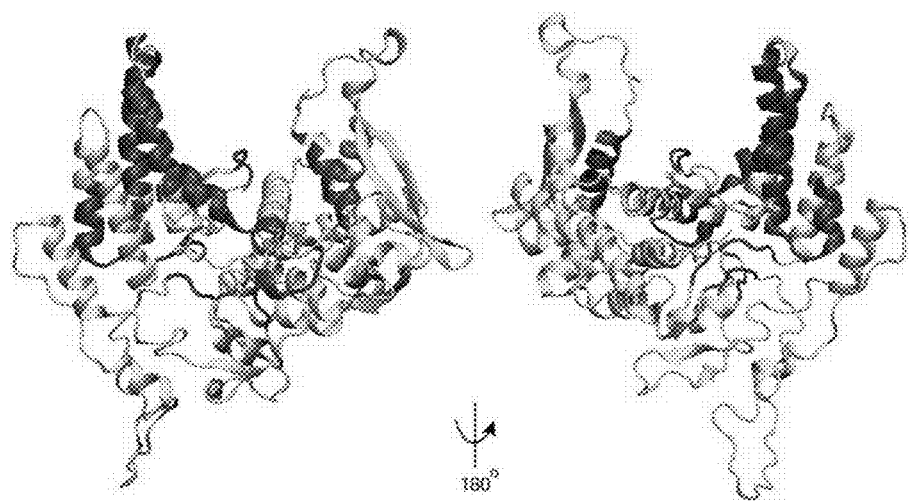
FIG. 5: Nucleoprotein of type-A Influenza virus whose amino acids corresponding to the slot intended for attachment the RNA are represented as dark.

According to a fifth aspect, the invention relates to a process for identifying a compound having the property of binding to the binding domain of the viral RNA to the nucleoprotein of the type-A Influenza viruses, said process comprising the following steps:

a) Modelling the (3D) three dimensional structure of the nucleoprotein of a type-A Influenza virus;

b) Generating a 3 dimension (3D) model of said binding domain of the viral RNA (FIG. 5) to said nucleoprotein from the structure obtained in a):

Said domain comprising the amino acids Arg65, Gln149, Tyr148, Arg150, Arg152, Arg156, Arg174, Arg175, Arg195, Arg199, Arg213, Arg214, Arg221, Arg236, Pro354, Arg355, Lys357, Arg361, Arg391, Lys184, Lys198, Gly212, Ile217, Ala218, Lys227, Lys229, Lys273 and Val353 of a sequence comprising the sequence SEQ ID No 1 preferably any amino acid situated at a distance less than 5 Ångströms of said amino acids, and Said domain being delineated by two loops, the first loop comprising the amino acid residues Glu73 to Lys90 and the second loop comprising the amino acid residues Gly200 to Arg214 of a sequence comprising the sequence SEQ ID No 1, c) Screening one or several compounds after the 3D model of the binding domain according to b);

d) Identifying a compound which may bind to a site forming a sphere of at least 12 Ångströms (Å) in diameter centred on the Tyr 148 residue, belonging to the binding domain of the viral RNA on said nucleoprotein, whereas said compound may inhibit the attachment of the RNA to the nucleoprotein of the type-A Influenza viruses and hence be used as a an inhibitor of viral replication.

In a preferred manner, a sequence comprising the sequence SEQ ID No 1 is the sequence SEQ ID No 2.

Preferably, the binding domain of the viral RNA to the nucleoprotein of a type-A Influenza virus as defined previously has the shape of a slot situated in the centre of the nucleoprotein as represented on FIG. 2.

By "(3D) three dimensional structure" is meant with reference to a protein the conformation of said protein in the space obtained from the primary sequence of that protein consisting in a linear succession of amino acids.

The (3D) three-dimensional modelling of the structure of the nucleoprotein of the type-A Influenza virus from the primary sequence of said protein is a method known to the man of the art who will be able to reproduce it with the methods at his disposal and known in the field. The modelling of the 3D structure of said nucleoprotein may notably be reproduced from the structure of the nucleoprotein of an Influenza virus such as the H1N1 strain accessible under the references PDB ID: 2IQH or MMDB ID: 43435 (Ye Q., Krug R. M. et al, 21 Dec. 2006, Nature, vol. 444 (7122), pp: 1078-82).

3D modelling of the binding domain according to the invention consists in designing using a modelling software the three-dimensional structure of said domain by addition, subtraction or modification of its constituents, for example amino acids, from the crystal structure of the nucleoprotein as defined previously.

The term "screening" defines the three-dimensional method which consists in testing several compounds with the binding domain of the viral RNA to the nucleoprotein of type-A Influenza viruses to identify a compound which can fix to said domain as well as its activity.

In another embodiment, the identification method according to the invention comprises a complementary stage e) consisting in testing in vitro the capacity of a compound identified according to stage d) in inhibiting the attachment of the viral RNA to the nucleoprotein as well as viral replication.

In vitro tests so as to determine the capacity of a compound to inhibit the attachment of the viral RNA to the nucleoprotein as well as the treatment efficiency of a viral infection caused by a type-A Influenza virus are exemplified below in the present application and are known to the man of the art.

In a preferred manner, the identification method according to the invention moreover includes a stage (f) comprising selecting such a compound as an inhibitor of viral replication.

The following examples detail the invention with reference to various methods. No limitation of the invention should be considered in the light of the detail of these examples. The invention comprises any embodiment which may include details not mentioned explicitly in the following examples, but that the man of the art will be able to find without unreasonable effort.

EXAMPLES

1) Method of Identifying Compounds Capable of Binding at Said Linking Domain of the Viral RNA to the Nucleoprotein of Influenza a Virus The screening according to the invention comprises several stages, all performed in silico by molecular modelling and detailed thereunder. This screening enables to identify potentially molecules which inhibit the attachment of the viral RNA to NP. These molecules are extracted from commercial chemolibraries, in the present case, the chemolibrary used was the Sigma catalogue.

The modelling is based on the crystallographic structure of the nucleoprotein (NP) with references PDB ID: 2IQH or MMDB ID: 43435 (Ye Q., Krug R. M. et al, 21 Dec. 2006, Nature, vol. 444 (7122), pp: 1078-82) and to which the missing residues have been added. This structure was minimised before the screening performed using the Discovery Studio commercial software accessible at the following address: http://accelrys.com/products/discovery-studio/structure-based-design.html, by using the Sigma (version 2008) catalogue as a chemolibrary. The 2D coordinates supplied have been transformed into 3D coordinates necessary to the software. The sequence of the nucleoprotein corresponds to the sequence SEQ ID No 1.

The are targeted in NP consists of a sphere of 12 Å radius centred on the residue Y148. Y148 enables to "dock" the inhibitor by type $\pi$-$\pi$ stacking interactions. This sphere moreover includes the loaded residues R361 and R152 forming electrostatic bonds or H bonds with the inhibitor, in some cases, the residues R150 and Q149 are also involved in H bonds. The simulations of molecular dynamics of NP and of two of its mutants R416A, R361A were performed using the NAMD software (Phillips, J. C et al (2005), Journal of Computational Chemistry, vol. 26, pp: 1781-1802) using the force field of the programme CHARMM27 (MacKerell, A. D et al, Biopolymers, vol. 56, pp: 257-265) based on the published structure of the H1N1 nucleoprotein (2IQH).

The missing portions in this crystallographic structure were generated using SWISS-MODEL. The solvent was treated explicitly by the model (TIP3P) for the water molecules (Jorgensen, W. L et al, 1983, Journal of Chemical Physics, vol. 79, pp: 926-935). The A monomer of NP was centred in a water cube of 155.4 Å a side. The electrostatic interactions were calculated without being truncated by the Ewald algorithm and the system was neutralised by adding 16 chloride ions (Darden, T., et al., 1993, Journal of Chemical Physics, vol. 98, pp: 10089-10092). The van der Waals interactions were cancelled progressively between 10.0 Å and 12.0 Å. The hydrogen atoms were generated by the SHAKE algorithm (Ryckaert, J. P et al, 1977, Journal of Computational Chemistry, vol. 23, pp: 327-341), iterations of movement equations by 2 fs-step were produced by Verlet integration of the velocities. An algorithm for minimising the energy gradient was used and the molecules of the solute (protein) were restricted to their initial position by a force of 50.0 kcal/mol/Å2, so as to generate a potential energy gradient RMS of 0.2 kcal/mol/Å. These constraints were cancelled and the minimised potential energy until the gradient is smaller than 0.1 kcal/mol/Å. The system was heated to 300 K within 60 ps. The simulations of molecular dynamics were used to balance the system for 1 ns, then five trajectories of 10 ns each enabled to generate NP WT the structures (dark) and its mutant R361A (clear) (FIG. 1).

The molecular modelling was used to define and analyse the structure of the monomeric form of NP, based on the structure obtained by crystallography. In this structure, the position of the flexible portions has not been solved and the modelling has added these missing flexible loops generated using SWISS-MODEL.

The mutated proteins R416A and R361A were created from the structure of the wild-type (wt) protein. The molecular dynamics of each of the three proteins, wt, R416A and R361A were simulated for five independent trajectories for 10 ns ($10^{-8}$ s) per 2fs-step ($10^{-15}$ s) to understand how the long distance interactions in NP are regulated and which induce modifications in the association of the RNA in the mutants R361A and R416A. The dynamics of these proteins placed in boxes of explicit solvent was analysed by circulating the mean fluctuations R416A (root mean squared fluctuations (RMSF)) of the protein skeleton during all the trajectories for 50 ns.

Figure 3:
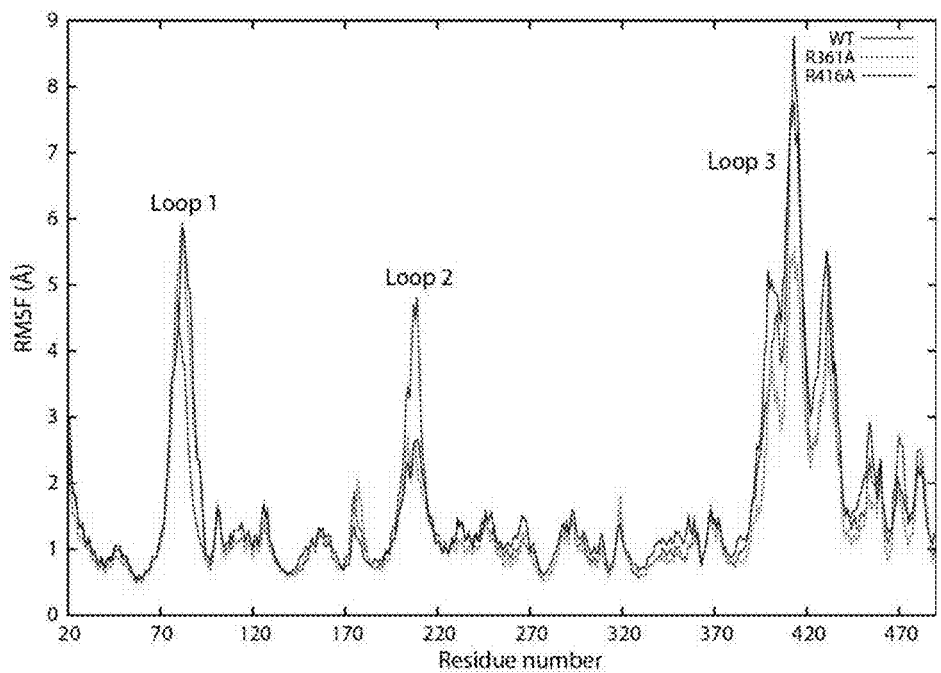
FIG. 3: Root Mean Square Fluctuation (RMSF) of the nucleoprotein NP and of the mutants R361A and R416A.

FIG. 3 shows the existence of 4 flexible areas possessing high dynamics and hence a flexible RMSF significantly higher than the rest of the protein. These are three flexile loops, whereas the first two surrounding the attachment slot of the RNA to one of the NP faces, Glu73 to Lys90 (loop 1)

and Gly200-Arg214 (loop 2). The third loop is situated on the other NP face and corresponds to the oligomerisation domain (402-428) of a monomer entering the neighbouring monomer within the trimer in the crystallographic structure. It is interesting to note the significant decrease of the mean fluctuation of the loop 2 of the mutants R416A and R361A with respect to that of the NP. These modifications of flexibility of the loop 2 are correlated with a small increase of the fluctuations of the loop 1 in mutants with respect to the wild-type protein. Modifications of the dynamics of the oligomerisation loop (loop 3) were observed in parallel, whereas this area of R416A becomes more mobile than NP, in agreement with the absence of oligomerisation of that mutant. The loop 3 of the mutant R361A becomes less mobile than NP, suggesting a better oligomerisation capacity, which correlates well with an increased proportion of this dimeric mutant with respect to the wild monomeric form.

FIG. 1 has a structure representative of the wild NP (dark): the wt amino acids: the R361 and R416 are in the attachment slot of the RNA and in the oligomerisation loop 3 respectively. The loops 1, 2 and 3 of the mutant R361A are superimposed in clear colour. It can be clearly seen that the loop 1 of the mutant R361A is quite close to the loop 2, this proximity is stabilised by a salt bridge between Glu80 and Arg208, in agreement with the RMSF decrease of the loop 2 of R361A. This contrasts with the wide and open cavity observed in the wild-type protein, which can easily accommodate an RNA. These observations are also found in the NP trimer (16). The loops 1 and 2 of NP WT could also help hang the RNA and guide it towards its attachment slot. Hence, when the distance between the loops 1 and 2 becomes small in R461A and R361A, the clap formed by both these loops becomes too narrow to adapt to the size of the RNA. The consequence is to reduce the accessibility of the RNA to its attachment slot in mutants compared with that of the wild-type NP. R416A and R361A indeed exhibit a smaller affinity for the RNA than that of NP and a lower association velocity as well. The changes noted in the structure of the loop 3 of R361A compared to that of NP as well as the mutation is introduced on the other face of the protein (in the attachment slot of the RNA) are in agreement with the long-distance interaction hypothesis in NP. These data are published in the article: Tams B, Chevalier C, Richard C-A, Delmas B, Di Primo C, et al. (2012) Molecular Dynamics Studies of the Nucleoprotein of Influenza A Virus: Role of the Protein Flexibility in RNA Binding. PLoS ONE 7(1): e30038. doi:10.1371/journal.pone.0030038

Figure 4:
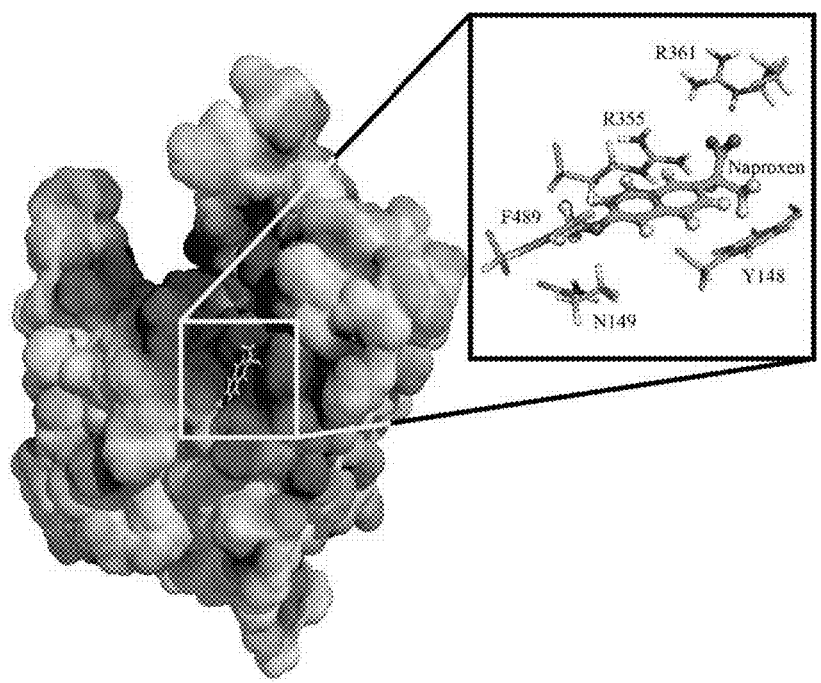
FIG. 4: Attachment of the Naproxen in the attachment slot of the nucleoprotein RNA and residues involved in the interaction, both by forming electrostatic with R361 (R355) or polar (N149) and hydrophobic bonds with Y148, F489.

FIG. 4 shows the attachment of Naproxen in the attachment slot of the RNA of the nucleoprotein (representation indicating the electrostatic potential, whereas the dark blue areas are charged positively and hence enable the attachment of the RNA); the zoom in the right portion shows the residues involved in the interaction, both by forming electrostatic with R361 (R355) or polar (N149) and hydrophobic bonds with Y148, F489.

2) Protocol Demonstrating the Attachment of the Naproxen and of the Triazole to the Nucleoprotein in Competition with the Viral RNA a) Surface Plasmon Resonance Test The first test conducted to demonstrate the attachment of the Naproxen in competition with the viral RNA to the nucleoprotein of sequence SEQ ID No 2 is a surface plasmon resonance test (BIOCORE 3000). The manipulation was performed according to the indications of the manufacturer (BIACORE SA).

A fragment of viral RNA was fixed to a gold chip covered with Dextran with streptavidin which binds quasi irreversibly the biotinylated end of the RNA fragment. The attachment of the RNA fragments to the gold chip was carried out in PBS. The signals were measured using 300 mM NaCl, 20 mM Tris-HCl puffer also contained 0.025% P20 surfactant with a 7.4 pH and a 25° C. temperature.

The sequences of the viral RNA fragments used are listed in the example 4.

The nucleoproteins were injected at concentrations from 4 to 1000 nM. The measurements were conducted at a temperature of 25° C. The samples were injected at a 25 µl/min flow rate.

Figure 6:
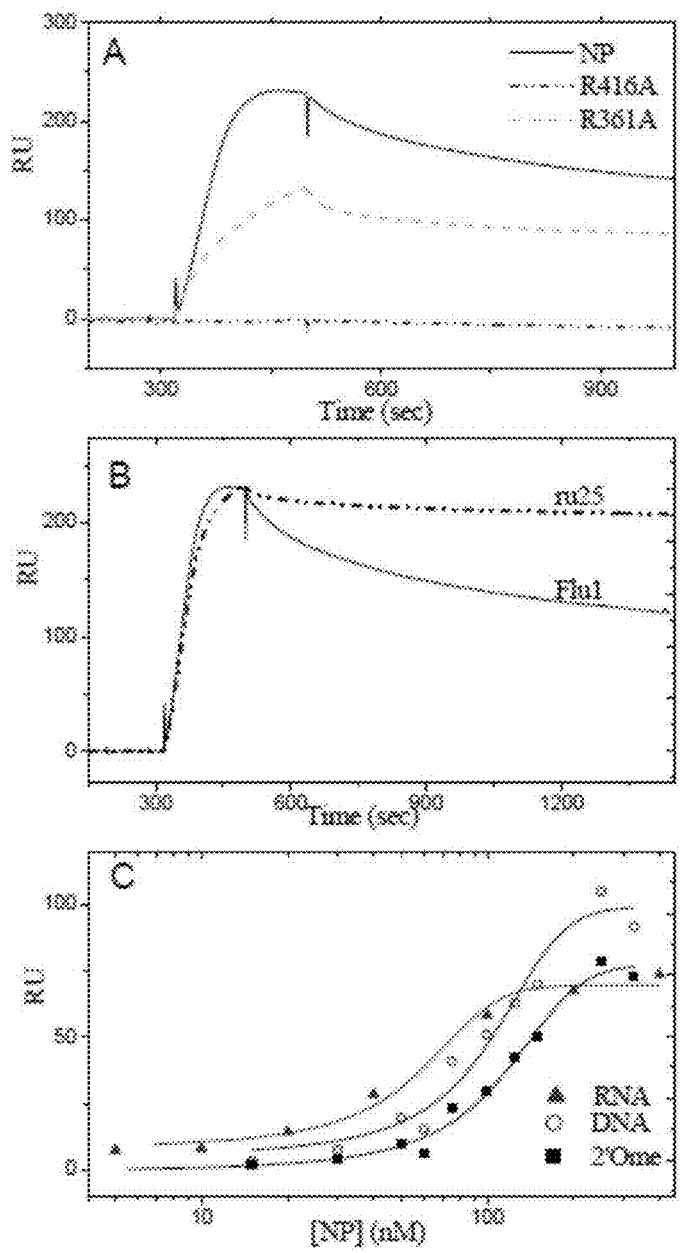
FIG. 6: Detection of signals resulting from the attachment of NP or of R416A and R361A mutants to single-stranded RNAs.

The binding of the nucleoprotein to the RNA caused a change in the refractive index proportional to the molecular weight of the protein and the concentration of the protein up to saturation (see example 4 and FIG. 6).

By comparing the signal obtained in the presence of NP WT on its own with the signal obtained after addition Naproxen to the wild-type protein, a signal decrease associated with the presence of Naproxen was observed contrary to an attachment of the nucleoprotein to the biotinylated RNA in the sole presence of the protein, the nucleoprotein does not fix any longer to the biotinylated RNA but has formed a complex with Naproxen, thereby pointing to a competition of Naproxen with the attachment of the protein to the viral RNA (FIG. 16A).

b) <<Molecular Beacon>> Test

A second test using an oligonucleotide called "molecular beacon" has been developed to show the attachment by competition of Naproxen to the nucleoprotein of SEQ ID No 2 (see diagram 18).

A beacon is an oligonucleotide with a quasi-palindromic sequence forming a hairpin and whose ends 5' and 3' have been modified by a fluorophor and a quencher. The beacon used here is a beacon with a sequence SEQ ID No 8 whose end 5' is grafted with a chromophore Vy5 and whose 3' by a DAPCYL quencher.

In the absence of protein, fluorescence is quenched: the fluorophor was close to the quencher when the oligonucleotide was paired. As nucleoprotein preferably fixes to single-stranded RNAs, its attachment to the beacon has caused the hairpin to open, which translates by increased fluorescence, whereas both ends 5' and 3' become far apart from each other.

This test has hence enabled to track by fluorescence the attachment of the protein quantitatively.

It has been observed that in the presence of Naproxen, fluorescence decreases: as nucleoprotein fixes to Naproxen and not to the RNA, the hairpin ends of the latter have not been spread apart by the competition of Naproxen preventing the attachment of the nucleoprotein to the RNA.

3) Directed Mutagenesis Approach Demonstrating that the Mutation of the NP Residues Necessary to the Attachment of Naproxen (N) Abolishes the Inhibition.

Figure 16:
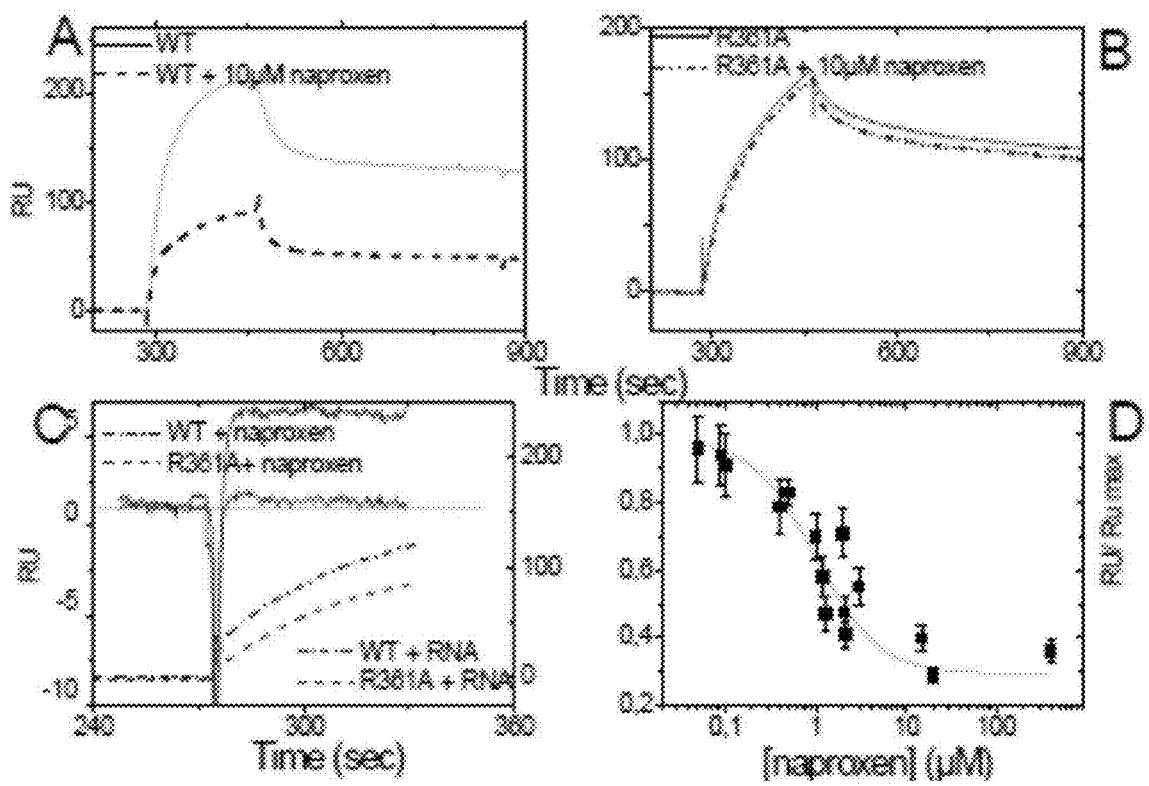
FIG. 16: Competition of Naproxen with the association of RNA to NP

The surface plasmon resonance is as described in example 2) has been carried out with mutated proteins at the amino acids R361A and Y148A. It has been observed that Naproxen does not compete with the RNA any longer, as expected by the interactions defined by molecular modelling (FIG. 4). When a mutated protein is used, in particular R361A and Y148A, Naproxen does not compete with the RNA any longer. The amino acids R361 and Y148 are hence essential for the attachment of the RNA or of Naproxen to the nucleoprotein of the Influenza A viruses (FIG. 4, FIGS. 16 A and B and Table 2 page 47).

4) Characterisation of the NP Association with RNA and Correlation with NP Oligomerisation Association Kinetics of NP and of R416A and R361A Mutants with Single-Stranded RNAs The association kinetics of nucleoprotein NP and of R416A and R361A mutants with single-stranded RNA were tracked by surface plasmon resonance (SPR) as described in example 2. The association and dissociation velocities of NP with the same DNA, RNA and RNA/2'-O-methyl sequence were compared. The results are regrouped in table 1 with:
- The Flu1 24-mer sequence of DNA nature corresponds to SEQ ID No 5:
- The Flu1 24-mer sequence of RNA nature corresponds to SEQ ID No 6:
- The Flu1 24-mer sequence of 2'-O-methyl RNA nature corresponds to SEQ ID No 6 with the modified ribose sugar so that it carries a methyl moiety in position 2'
- The rU25 25-mer sequence of RNA type corresponds to SEQ ID No 7

TABLE 1

Association and dissociation velocities of NP with the same DNA, RNA and RNA/2'-O-methyl sequence

| Sequence | NP | Nature | $k_{on}$ $M^{-1}s^{-1}$ | $k_{off}$ calculated $s^{-1\#}$ ± 25% | Kd (nM) | RU(plateau)/ RU max* |
|---|---|---|---|---|---|---|
| Flu1 24-mer | wt | DNA | $1.1 \pm 0.2 \times 10^5$ | $1.1 \times 10^{-2}$ | 105 ± 15 | 0.9 |
| Flu1 24-mer | wt | -2'Ome RNA | $9.5 \pm 1.7 \times 10^4$ | $1.1 \times 10^{-2}$ | 115 ± 10 | 0.74 |
| Flu1 24-mer | wt | RNA | $1.8 \pm 0.3 \times 10^5$ | $0.7 \times 10^{-2}$ | 41 ± 7 | 0.65 |
| rU25 25-mer | wt | RNA | $8.5 \pm 1.2 \times 10^4$ | $0.4 \times 10^{-2}$ | 45 ± 8 | 1.1 |
| Flu1-24-mer | R361A | RNA | $3.1 \pm 0.5 \times 10^4$ | $1.2 \times 10^{-2}$ | 400 ± 100 | 0.9 |
| Flu1-24-mer | R416A | RNA | 500 ± 150 | $0.5 \times 10^{-2}$ | 10 ± 3 μM | ~0.66 |

The data represent the average of 3 experiments.
*The ratio of the signal observed at high protein concentrations to the expected maximal RU value was calculated on the basis of the molecular weight of NP and that of a partially complementary oligonucleotide to the chip-immobilised FLU1 probe.
The values of $k_{off}$ were calculated from the experimental values of Kd and $k_{on}$.

These results show the formation of RNA-protein complexes with 1/1 stoichiometry. These monomeric proteins hence fix the RNA first and oligomerisation takes place at a later stage. The wt NP association results in the rapid formation of a NP-RNA complex with 1:1 stoichiometry. Table 1 shows a decrease by a factor 10 of the affinity of R361A compared with that of wild-type NP.

FIG. 6 compares the signals resulting from the attachment NP to those obtained with the same concentration (300 nM) of R416A and R361A. The mutant R416A does not fix to Flu1-RNA, but an affinity of Kd=10±3 nM can be determined by using concentrations of R416A 1-100 nM. See publication: Bogdan Tams, Olivier Bakowiez, Sylvie Chenavas, Leandro Estrozi, Christophe Chevalier, Christiane Bourdieu, Julie Bernard, Mohammed Moudjou, Bernard Delmas, Carmelo Di Primo, Rob W H Ruigrok and Anny Slama-Schwok: Multiple oligomerisation paths of the nucleoprotein from Influenza A virus (2012) Biochemistry: 94 776-785. doi.10.1016/j.biochi.2011.11.009)

Correlation Between the Association Velocity of NP to the RNA and the Apparent Velocity of Oligomerisation of NP and of its Mutants.

Additional techniques such as dynamic light scattering (DLS) and electronic microscopy (EM) were used for tracking the slow oligomerisation process and to carry out a correlation between the association velocity of NP to the RNA and the apparent velocity of oligomerisation of NP and of its mutants. The effect of the length of the oligonucleotide and the nature of the nucleic acid (DNA vs RNA)) on the oligomerisation kinetics of NP or of its mutant R361A were tested. The EM images are in accord with the time scales in which the oligomerisation of NP takes place in the presence of RNA and define the shape of the RNA-formed oligomers dependent on the length of the RNA.

Figure 7:
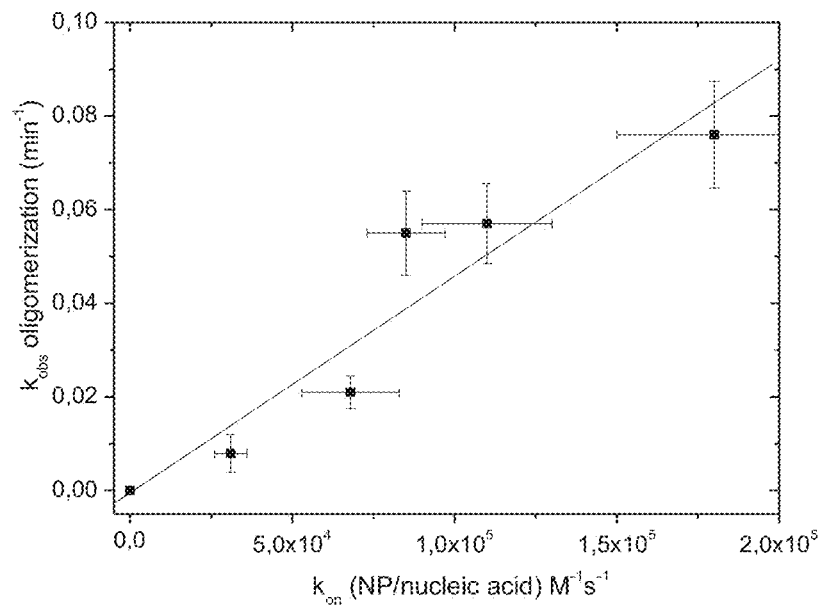
FIG. 7: Correlation between the speed formation of the NP complex or of the R416A and R361A mutants with the apparent velocity of oligomerisation

The attachment velocity of NP to the RNA and the velocity of oligomerisation of NP and of both its mutants in the presence of RNA are well correlated. The formation velocity of the 1/1 NP complex or its R416A and R361A mutants is correlated with the apparent velocity of oligomerisation (FIG. 7). The abnormal association of R416A to the RNA is associated with a defect of oligomerisation. Similarly, the decrease of the association velocity of R361A is also associated with a low oligomerisation velocity (determined by adjusting with an exponential function the experimental points obtained by dynamic light scattering with apparent size increase from (6.8±0.5 nm) to (11±1 nm) in relation to time). With NP as well, when the association velocity to the RNA increases, the association velocity of monomeric NP to oligomers increases. This suggests a "crosstalk" between the attachment domain to the RNA and the oligomerisation loop.

5) In Vitro Test Protocol of the Antiviral Effect of N on MDCK Cells Infected by the Influenza A/33/WSN Strain.

Figure 8:
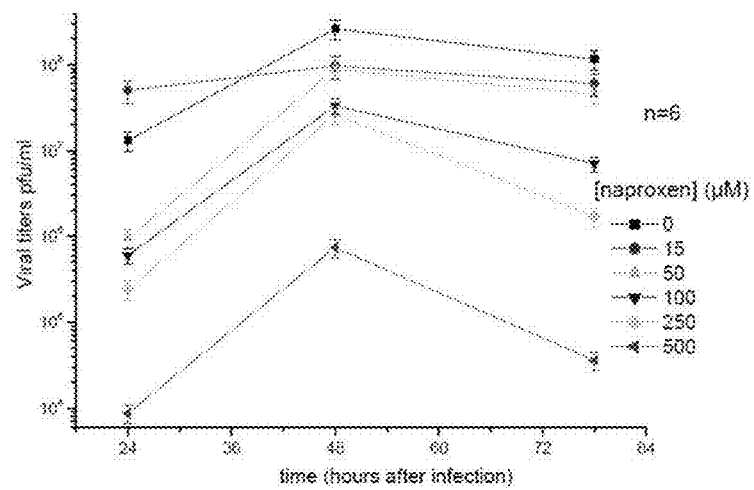
FIG. 8: Decrease in viral titer of MDCK cells infected by a type-A/WSN Influenza virus with a $10^{-3}$ multiplicity of infection (MOI) in the presence of Naproxen added to t=0.

MDCK were placed into culture at 80% confluence at 37° C. in the presence of 5% $CO_2$ and antibiotics in a minimal medium (EMEM, Sigma, L-glutamine, Gibco and $NAHCO_3$ 7.5%) in the presence of 5% foetal veal serum on 12-well plates ($0.32 \times 10^6$ cells/well) for 24 hours. The cells were rinsed by serum-less medium and the inoculum (400 μl) of Influenza A/WSN/33 virus was placed to adsorb for one hour on the cells at a $10^{-3}$ multiplicity of infection (MOI) (kinetic study) or MOI 1 or 5 (visualisation of the effect after 24 h and comparison with another antiviral). After rinsing the inoculum, the cells were placed to incubate with different concentration of Naproxen (1 to 500 μM). Non-infected cells were also subjected to incubations in parallel with variable concentrations of Naproxen. The replicating virus was excreted in the culture supernatant from which samples were taken 24, 48 and 72 hours after infection (FIG. 8). The viral titer of these samplings was measured using the lysis plate method. Briefly, MDCK cells were put in contact with serial dilutions of the cellular supernatants and included in carboxymethylcellulose. The lysis plates generated by the virus were revealed by attachment of the cells to formaldehyde and violet crystal marking. Counting the number of plates according to the dilution of the cellular supernatants enabled to establish the viral titer.

The results of FIG. 8 present an average of the results over 6 experiments conducted at growing concentrations of Naproxen. Thus, it can be observed that the greater the concentration in Naproxen, the quicker the decrease of the viral titers.

Figure 9:
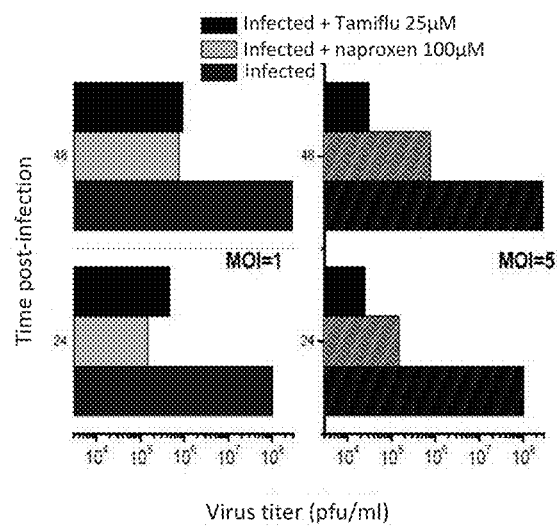
FIG. 9: Comparison of the effect of Naproxen-Tamiflu on MDCK cells infected by an Influenza A/WSN virus.
Figure 10:
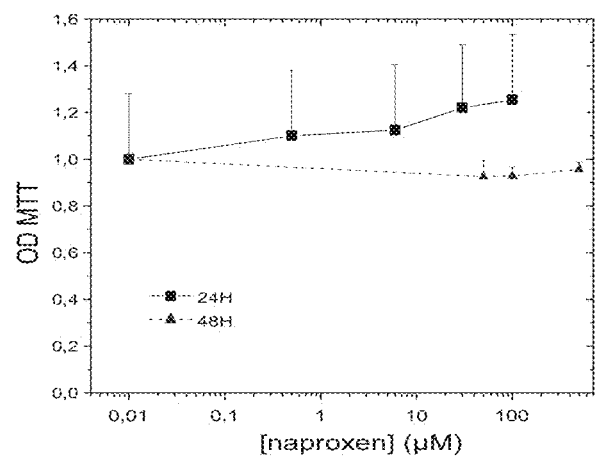
FIG. 10: Test of MTT cell viability on A549 cells with Naproxen

Certain experiments were conducted in parallel in the presence of Naproxen and of Tamiflu to compare their antiviral effect. FIG. 9 shows that the viral titer decreases similarly with a Naproxen treatment or a Tamiflu treatment in the case of a multiplicity of infection MOI=1 and demonstrates the antiviral efficiency of Naproxen comparatively with Tamiflu.

6) In Vitro Test Protocol of the Antiviral Effect on Human Lung A549 Cells Against a H1N1 Viral Challenge with WSN Strain by Immunofluorescence The A549 cells were placed into culture for 24 hours on microscope lamellae deposited at the bottom of P6 plate wells. The same protocol as above was followed for immunofluorescence measurements. The cells were fixed to paraformaldehyde 3 hours or 24 hours after infection and a primary marking was made by adding an anti-NP mouse monoclonal antibody. The addition of a fluorescein marked secondary anti-mouse antibody (FITC) enabled direct reading by fluorescence. The cells were also treated with DAPI, enabling nucleus marking. This double marking enabled to reveal the nuclear localisation of the NP and its possible modification associated with the presence of antivirals. As in the previous experiments, kinetics were conducted at different times after infection, 3 hours and 24 hours and different MOI of 1.5 and 10.

The results have shown that Naproxen has not modified the localisation of nucleoprotein, which is essentially nuclear at time t=3 hours whereas NP was found to diffuse in the cytoplasm and the nucleus at t=24 hours. The presence of Naproxen (50 to 100 µM) reduced the number and the size of the infectious outbreaks in the cell layer and the number of dead cells. Numerous double nuclei were found to be present in the cells treated at high Naproxen concentrations, in agreement with an increase in the number of cells in phase S reported in the literature.

7) Protocol of the MTT Cell Viability Test Showing the Absence of Cytotoxicity at the Concentrations Used The MTT test (based upon the use of a tetrazolium salt) is a cell viability test relying on the mitochondrial activity. This salt is reduced by the mitochondrial dehydrogenase succinate of living cells in formazan, which causes a colour change from yellow to blue-violet which may be quantified by an absorbance change at 560 nm. We used this test to show the non-toxicity of our compounds in the presence of human lung A549 cells. 30,000 cells per well were seeded on plates 24 hours before the beginning of the experiment. The antivirals were added at concentration of 1 to 500 µm to the cells for 24 H or 48 H before revelation. The MTT was then freshly dissolved in PBS (5 mg/ml) then added (20 µl per well) and incubated for one hour at 37° C. The cells were rinsed and dried before addition of 100 µl DMSO per well. Reading was done at 560 nm by subtracting the background noise at 670 nm.

Figure 19:
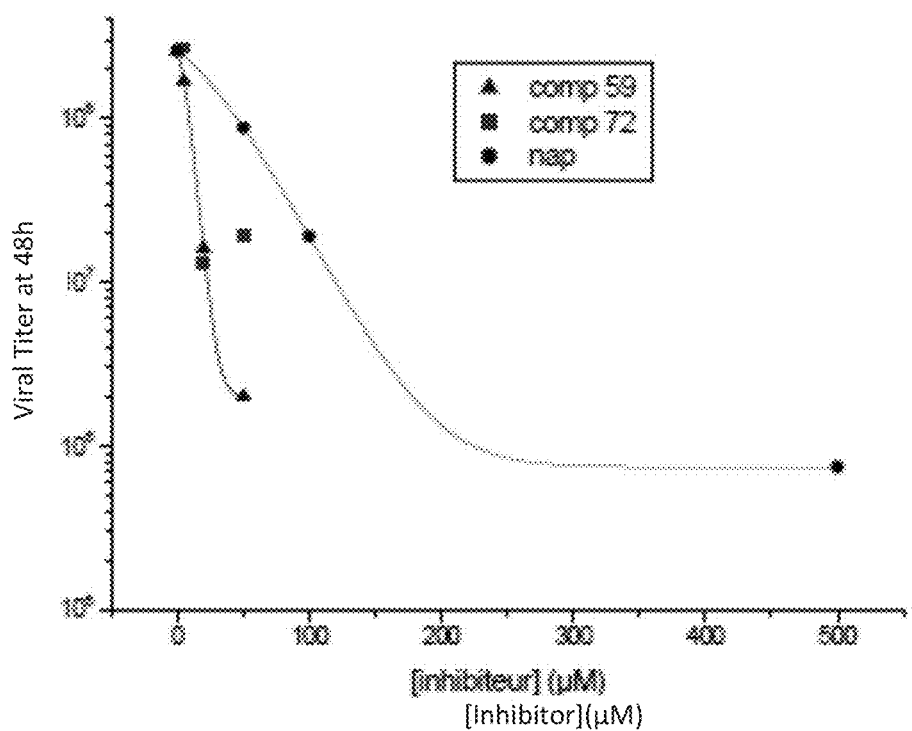
FIG. 19: Measurement of the viral titer in the presence of different inhibitors: compound 59, compound 72 and Naproxen.

FIG. 19 shows that the Naproxen is not toxic for A549 cells after 48 H incubation and that on the contrary, it promotes their growth, in particular after 24 H.

8) In Vivo Test Protocol of the Effect of a Treatment with Naproxen in Mice

The antiviral efficiency of Naproxen was tested in vivo on 6-week Balb/C female mice (kept in the animal ward for week without any particular treatment). On day j+7 of their arrival, the mice were inoculated or not with 2000 pfu/ml Influenza A/PR8/34 virus (10 mice per condition) by intranasal route. Possible cytotoxic effects of Naproxen were tested by comparing non-treated mice (without virus) with mice treated once a day at 1 mg or 3 mg doses per mouse (in the absence of virus). The virus was inoculated by intranasal route under anaesthesia (ketamine/xylazine). Naproxen was administered just after per intraperitoneal route (1 or 3 mg, former data) and (1, 3, 4, 8 mg, new data) in 50 µl physiological serum).

Figure 11:
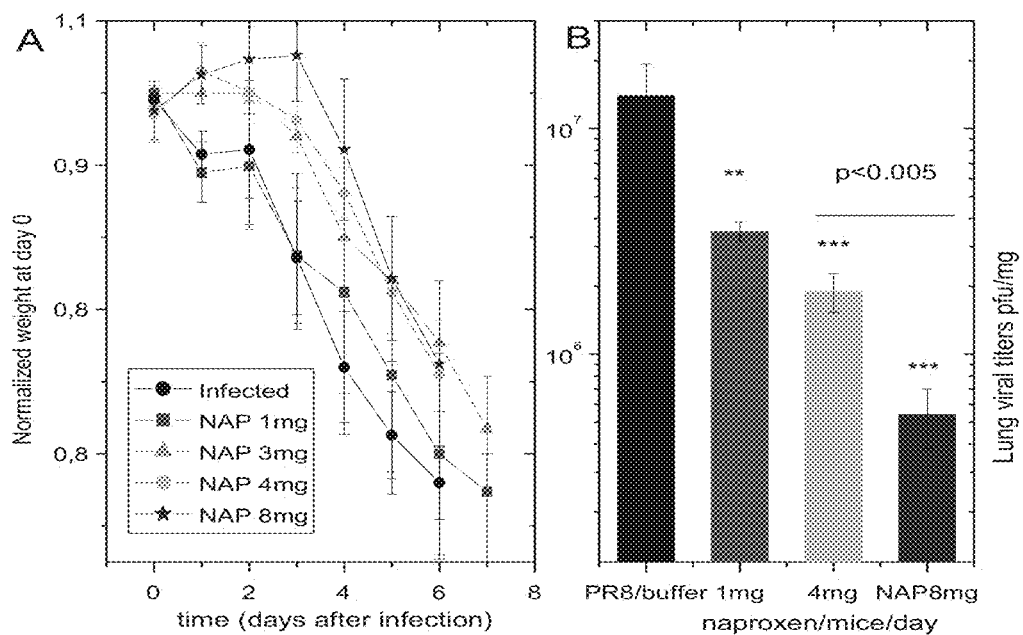
FIG. 11: Effect of naproxen treatment in mice. A: weight loss normalised to the initial weight on the day of infection; B: viral titer in the lungs of mice 7 days after infection. Representative results of 3 experiments, 7 to 10 mice are used for each naproxen concentration and for the control in each experiment; intranasal infection with 2000 pfus by the A/PR8 virus (H1N1)
Figure 12:
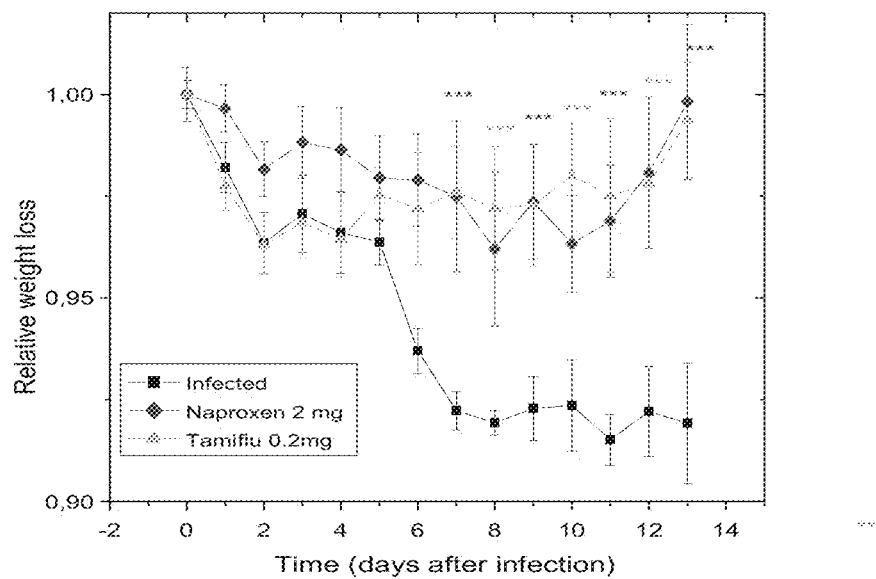
FIG. 12: comparison of the average weight loss by 50 pfu/ml of type-A/PR8 Influenza virus without and with IP 2 mg injection of naproxen/mouse/day or 0.2 mg Tamiflu/mouse/day.

The weight curve of each mouse is recorded every day, for 7 days. The weight curves are represented on FIGS. 11A and 12 and were related to the weight measured on the day of infection and correspond to average weights on a sample of 10 to 15 mice. In the case of FIG. 11A, the figure is representative of 3 experiments, conducted with a viral load of 2000 pfu PR8 administered by intranasal route. FIG. 12 is representative of 2 experiments with a viral load of approximately 50 pfu (0.01LD50). The mice were sacrificed after a week without noting any deaths. A bronchoalveolar wash was conducted before removing the lungs to determine the viral titer. A sample of bronchoalveolar washes was deposited on a slide by centrifugation using a cytospin on a slide. The fixed cells were marked by May Grunwald staining, to determine the presence or not of a lung inflammation related to viral infection, particularly reflected by a change in the total number of cells. On FIG. 13, A3 corresponds to lungs of infected mice, F2 corresponds to lungs of uninfected mice, E1 corresponds to mice treated with 3 mg Naproxen. The number present under the indication of the type of mouse analysed in FIG. 13 corresponds to the index accounting for the weight loss. Thus, the mice E1 record respectively a 19% weight loss (indices 0.79) whereas the mice A3 record a 31% weight loss (index 0.69) comparatively to a mouse whose lungs are not infected (index 1.01 i.e. 101% of the initial weight).

Figure 13:
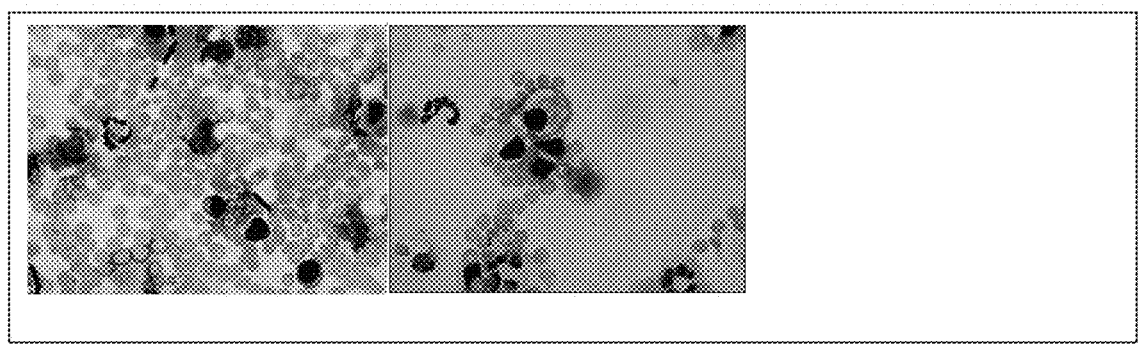
FIG. 13: Observation of pulmonary cells, of infected (A), infected and treated (B), non infected (C) cells.

We could also note a change in cellular populations, mainly composed of alveolar macrophages in a healthy lung (F2), whereas the presence of neutrophils and of eosinophils as well as red blood cells is characteristic of bloody lungs infected by the virus (FIG. 13).

The lungs of the sacrificed mice were crushed and frozen to determiner the viral titers. The results shows a decrease of approximately a 100 factor by administration of 0.2 mg Tamiflu and a 42 factor by administering 2×4 mg Naproxen by IP route of the viral titer of the infected mice treated with 1 mg Naproxen with respect to the untreated infected controls (FIG. 11B).

9) Design of Naproxen Derivatives and Docking of Influenza Virus in the Nucleoprotein NP A second generation of compound derived from Naproxen was built: Construction of the derivative A of Naproxen, designated hereafter in the application as "derivative of Naproxen A" or "Naproxen A" to increase the affinity for NP by adding a negatively charged moiety (fragment-based design).

A stability test of the NP-Naproxen A derivative complex by MD simulations (10 ns) was then conducted.

The Naproxen A derivative was then modified into Naproxen B, c0, c1, c2 and c3 derivatives. The last three compounds correspond to a change in the OCH3 moiety (methoxy moiety of Naproxen). The in silico results of the Naproxen B, c1, c2 and c3 derivatives are not presented here.

Figure 14:
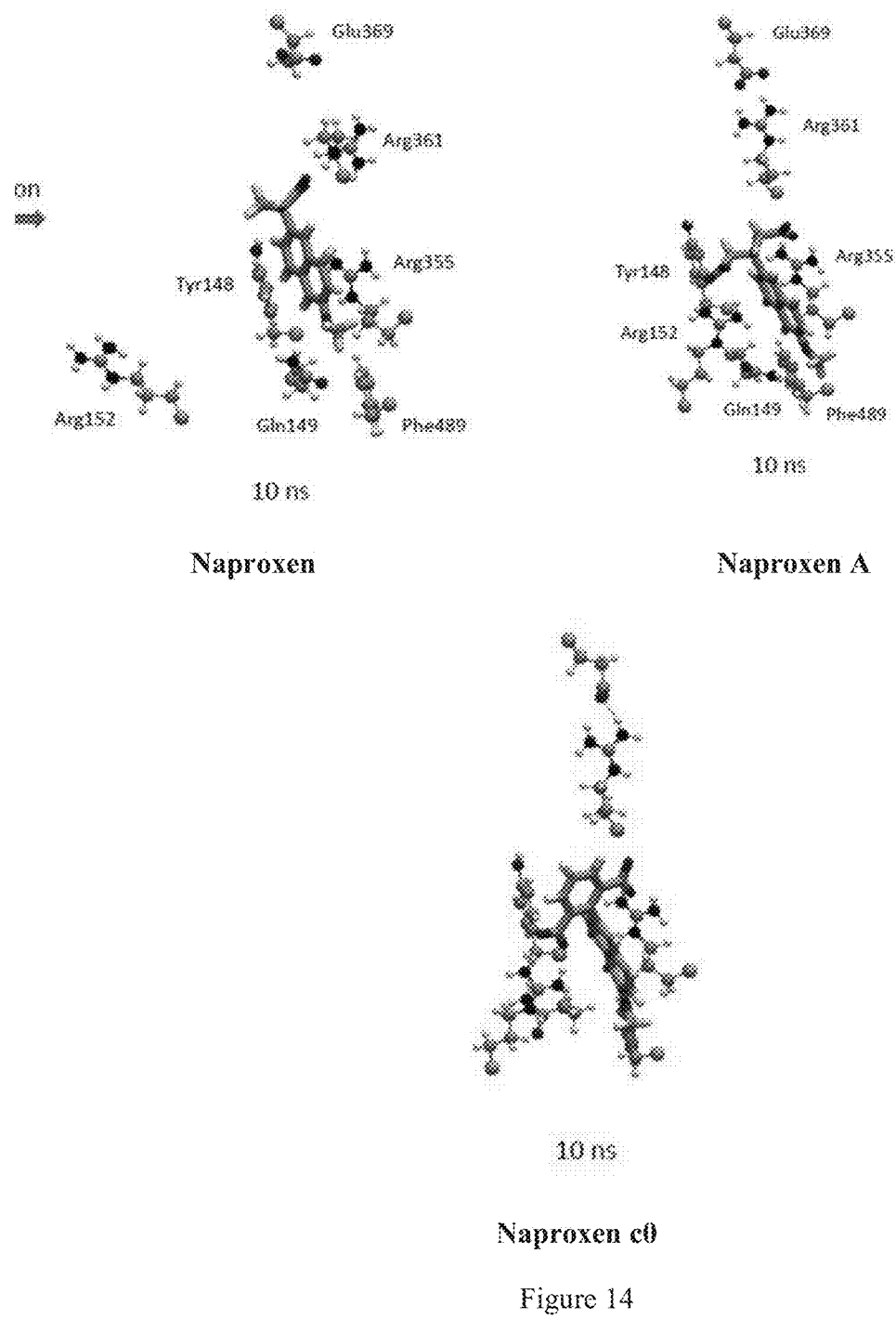
FIG. 14: Docking of the A and c0 Naproxen in the nucleoprotein of the Influenza A virus

FIG. 14 compares the Naproxen compounds, derivative of Naproxen A and c0 at the end of the 10 ns MD. The residues of NP involved in the interaction with the Naproxen A and c0 derivatives are: R355, R152, N149, lower interaction with Y148 or R361, in contrast with Naproxen.

Figure 15:
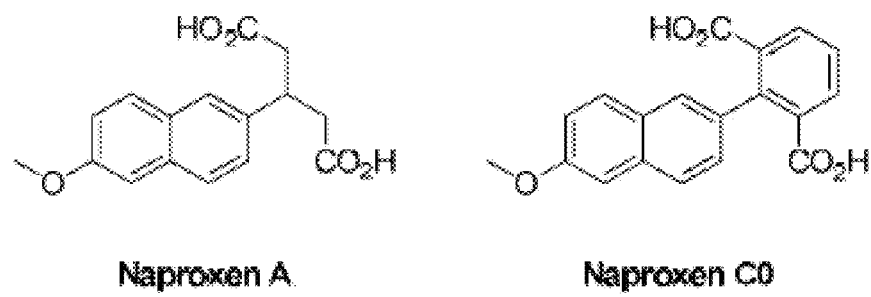
FIG. 15: Structure of the compounds of interest Naproxen A and Naproxen c0

The chemical formulae of the derivatives of Naproxen A and c0 are represented on FIG. 15.

10) Protocol of Chemical Synthesis of Naproxen Derivatives: Naproxen A and c0 Derivatives a) Synthesis of Naproxen A Naproxen A is synthesised in three stages according to diagram 1. 2-bromo-6-methoxynaphthalene 1, commercially available, is lithiated by n-BuLi and treated by DMF to produce 6-methoxy-2-naphthaldehyde 2 with a 90% yield. The substituted 3-naphthalenyl 3 glutaric acid or Naproxen A, is then obtained with a 65% yield in two stages by reaction of naphthaldehyde 2 with two equivalents of ethyl acetoacetate and a catalytic quantity of piperidine, followed by hydrolysis in the presence of aqueous potassium hydroxide in EtOH.

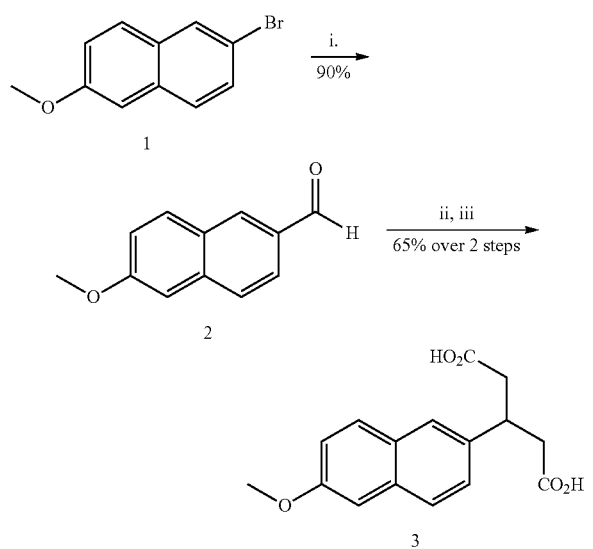

Diagram 1.

Synthesis of Naproxen A (compound 3). Reactants and conditions: i/ n-BuLi (1.12 equiv.), anhydrous THF, −78° C., 30 min then DMF (2.15 equiv.), −78° C. at room temperature; ii/ Ethylacetoacetate (2.0 equiv.), EtOH, piperidine (catalytic), 0° C. at room temperature, 3 days (yield 70%); iii/ aq. KOH (32 equiv., 24 M), EtOH, reflux, 3.5 hrs (yield 92%).

b) Synthesis of Naproxen C0

Starting from bromo-m-xylene 4, we have prepared the dimethyl 2-bromoisophthalate 6 intermediate by oxidation of the methyl moieties by $KMnO_4$ in a $tBuOH/H_2O^3$ followed by esterification of carboxylic diacid obtained 5 in MeOH in the presence of concentrated $H_2SO_4$ (Diagram 2, top). The dimethyl ester 8 of Naproxen C0 is synthesised by Suzuki coupling between 2-bromoisophthalate 6 and 6-methoxy-2-naphthaleneboronic 7 acid commercially available.

The conditions used, supplying the compound 8 with a poor 45% yield, should be optimised. Naproxen C0 (compound 9) is finally obtained after hydrolysis of the ester functions in aqueous LiOH and THF with a good yield (91%) and high purity (Diagram 2, bottom).

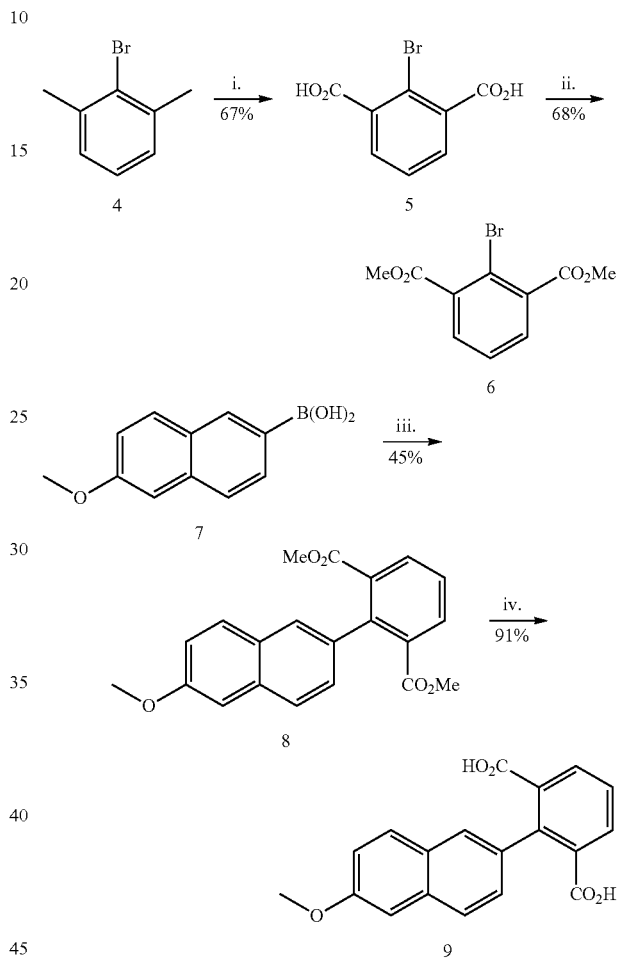

Diagram 2.

Synthesis of Naproxen C0 (compound 9). Reactants and conditions: i/ $KMnO_4$ (2.0 equiv.), $tBuOH/H_2O$ (1/1), reflux, 4 hrs, then $KMnO_4$ (2.0 equiv.), reflux, 16 hrs; ii/ MeOH, conc. $H_2SO_4$, reflux, 16 hrs; iii/ dimethyl 2-bromoisophthalate 6 (0.92 equiv.), $Pd(PPh_3)_4$ (0.03 equiv.), aq. $Na_2CO_3$ (4.2 equiv., 2 M), DME/EtOH, reflux, 16 hrs; iv/ aq. LiOH (7.2 equiv., 1 M), THF, reflux, 4 hrs.

11) Test Conducted In Vitro with NP Nucleoproteins of Wild Strains or Purified Mutants and the Naproxen Compound as Well as its Naproxen A and Naproxen c0 Derivatives Methods: surface plasmon resonance test (SPR) (see protocol above for the indirect method with RNA immobilised on a streptavidin chip and injection of NP +/−antiviral).

The direct association of Naproxen to NP was conducted using a CM5 chip and NP was immobilised there by coupling with the amines as indicated by BiaCore. The R361A or Y148A or R355A or R152A mutated proteins were attached similarly on another track of the same chip with a resonance unit comparable to that of NP, keeping a control track so as to subtract the non-specific effects. To check that proteins have not been denatured by surface immobilisation, RNA was injected in every case, testifying that these proteins remain at least partially active (FIG. 16C).

Figure 17:
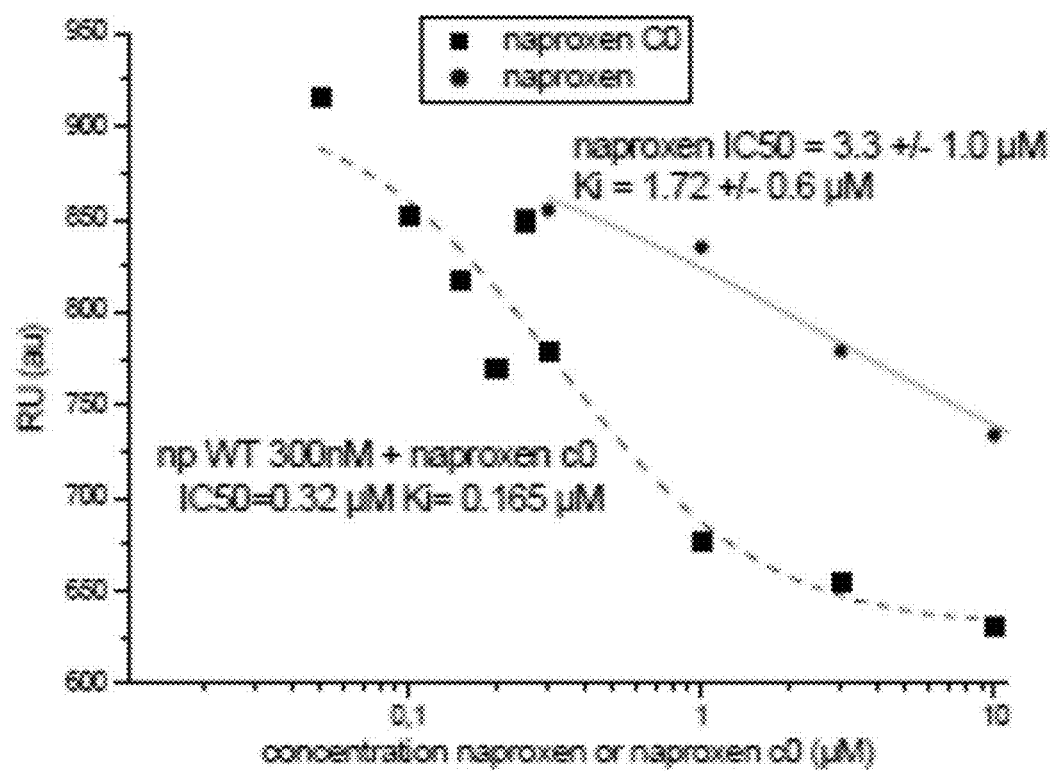
FIG. 17: Results of the surface plasmon resonance test for Naproxen and Naproxen c0

The results are described on FIGS. 16 and 17 as well as in table 2 thereunder.

Naproxen competes with the association of RNA with NP, whereas said competition is emphasised by the signal decrease of the NP-RNA complex, Panel A. This is not observed in the presence of mutated proteins in residues involved in the NP—Naproxen interaction, R361A (or Y148A), since the interaction of Naproxen with R361A is abolished by the mutation (Panel B), in agreement with the modelling.

The results are quantified, Panel D and table 2.

Panel C shows the direct attachment of Naproxen with NP bound to the surface but not to R361A, whereas both 2 immobilised proteins remain active and capable of binding the RNA. However, the signals are too weak for quantitative determination of Kds.

The SPR results show the improvement of Naproxen c0 (with respect to Naproxen) to compete with the association of the RNA to NP (lower Ki by approx. one order of magnitude) (FIG. 17 and table 2). Naproxen A has a biphasic effect, thereby introducing a difficulty in quantitative characterization of Ki.

As expected by modelling, the R152A mutation has no effect on Naproxen while it reduces the affinity of the Naproxen A and c0 derivatives (table 2). R361A abolishes the attachment of all the derivatives, which is anticipated for Naproxen. Naproxen does not fix to the R416A mutant, known to be an inactive monomer.

TABLE 2

In vitro inhibition of the binding of the viral RNA with
NP by Naproxen and its derivatives (SPR derivatives)

| Compound | Protein | Concentration range of ligand | IC50 |
|---|---|---|---|
| Naproxen | NP WT | 50 nM-50 µM | 3.3 ± 1.0 µM |
| Naproxen c0 | NP WT | 50 nM-50 µM | 0.32 ± 0.09 µM |
| Naproxen A | NP WT | | 0.2 ± 0.1 µM and ~2 µM |
| Naproxen | R152A | | 2.5 µM |
| Naproxen c0 | R152A | | 1.2 ± 0.1 µM |
| Naproxen A | R152A | | ~0.4 µM |
| Naproxen | R361A | | No binding |
| Naproxen c0 | R361A | | No binding |
| Naproxen A | R361A | | No binding |
| Naproxen | | | No binding |
| Naproxen | Y148A | | No binding |

12) Toxicity Test and Antiviral Effect of Naproxen and of its Naproxen A and Naproxen c0 Derivatives Conducted by MTT Tests, Measuring the Viral Titer The protocol followed corresponds to the toxicity test protocol as described above.

TABLE 3

Tests conducted on uninfected MDCK cells, measurement
of the concentration and of the toxicity of Naproxen
compounds and its Naproxen A and c0 derivatives

| Compound | Test conducted on uninfected MDCK cells | Concentration | |
|---|---|---|---|
| Naproxen | MTT 24 or 48 H | 2-500 µM | No toxicity |
| Naproxen c0 | MTT | 1-200 µM | No toxicity |
| Naproxen A | MTT | 1-200 µM | No toxicity |

TABLE 4

Test conducted on infected MDCK cells, 48 h after infection with
low multiplicity of infection (MOI) of H1N1 virus (wsn/33), by
the MTT test: measuring the effect of the Naproxen compounds and
its Naproxen A and Naproxen c0 derivatives at the concentrations
specified on cell viability and calculation of protection

| Compound | Test conducted on infected MDCK cells | MOI | Concentration of compound | Protection % |
|---|---|---|---|---|
| Naproxen | MTT 48 h | A/wsn/$10^{-3}$ H1N1 | 10 µM | 25 ± 2% |
| | | | 25 µM | 48 ± 2% |
| | | | 50 µM | 47 ± 2% |
| Naproxen A | MTT 48 h | A/wsn/$10^{-3}$ | 5 µM | 8 ± 1% |
| | | | 25 µM | 54 ± 4% |
| Naproxen c0 | MTT 48 h | A/wsn/$10^{-3}$ | 5 µM | 30 ± 3% |
| | | | 25 µM | 77 ± 5% |

TABLE 5

Test conducted on infected MDCK cells, 24 after infection
at different viral titers (MOI) of H3N2 virus: measuring
the cell viability at the specified concentrations of the
Naproxen compound and calculation of protection

| Compound | Test conducted on infected MDCK cells | MOI | Concentration of compound | Protection % |
|---|---|---|---|---|
| Naproxen | MTT 24 h | A/Udorn/1 H3N2 | 100 µM | 19 ± 2% |
| | | | 500 µM | 45 ± 2% |
| Naproxen | MTT 24 h | A/Udorn/$10^{-1}$ | 100 µM | 85 ± 2% |

The results show that Naproxen has an antiviral effect on the H1N1 wsn and H3N2 udorn strain according to the MTT tests. The results of the determinations of the viral titers in cells (wsn, FIG. 8) and in vivo (FIGS. 11 and 12) are already summed in the form of figure.

13) Docking of a Triazole Derivative, the L410 Compound, in NP

The L410 compound was docked at the nucleoprotein according to the protocol as described above.

The formula of the L410 compound derived from triazole is as follows:

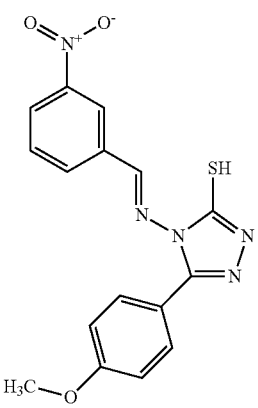

Compound L410

Further to this docking, it proves that the Influenza virus NP residues involved in the interaction with the L410 compound are as follows: R150, Y148, R361, Gln149.

Figure 18:
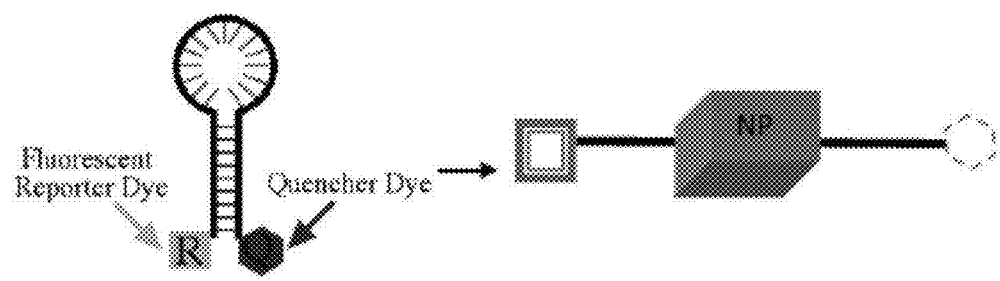
FIG. 18: Diagram of the fluorescence test

14) In Vitro Tests of the Efficiency of the Compound Derived from L410 Triazole on purified NP WT a) Fluorescence:

The fluorescence measurements were conducted using a Jasco fluorometer fitted with a sample holder thermostated at 20° C. A sequence forming a stem-loop was used: 5' AUA UAU AUC GAC AUA GAU AUA UAU 3' (SEQ ID No 9), whereas the underlined bases are paired and form the stem. This stem-loop possesses a fluorophor R=Cy3 in 5' and a quencher Q (dabcyl) in 3' (see FIG. 18). The attachment of NP induces the opening of the stem-loop, pushing R from Q, which translates in fluorescence enhancement. R is energised at 525 nm, fluorescence is collected between 535 and 650 nm. The corresponding excitation spectra were obtained at λem=580 nm, λexc varying between 440-570 nm. The samples were prepared at a concentration of stem-loop of 100 nM with and without NP (50 nM-3 μM) in 20 mM Tris at pH=7.4 containing 50 mM NaCl.

b) Surface Plasmon Resonance Experiments

The association kinetics of the NT-RNA complexes with and without antiviral could be obtained using a Biacore 3000 device with chips covered with streptavidin (SA, BiaCore) and conditioned as recommended by Biacore. The immobilisation of biotinylated RNA oligonucleotides on the streptavidin chip was conducted in PBS buffer. The kinetics were obtained in a 20 mM Tris-HCl buffer, pH=7.4 containing 300 mM NaCl and 0.025% P20 surfactant (BiaCore) at 20° C. Before their immobilisation, the oligonucleotides were denatured at 80° C. and re-natured at room temperature for one hour. The wild NP proteins or its mutants were injected at concentrations of 100 to 500 nM in the presence or absence of 50 nM and 20 μM antiviral, up to 300 μM in some cases. The samples were injected at a 25 μl/min flow rate.

c) Results:

The NP-L410 interaction was assessed by two indirect competition methods when the L410-NP complex is formed in competition with the NP-RNA complex.

SPR enables to track the protein, whereas fluorescence enables to track the marked RNA. Both these methods enable to assess a concentration at which there is 50% inhibition (50% of the NP-RNA complex is destroyed) IC50=0.2-0.3 ìM.

15) Cellular Toxicity and Antiviral Effect of Compounds Derived from Triazole by MTT Test a) Cell Viability According to the MTT Test:

A549 or MDCK cells ($3 \times 10^4$ cells/well) were placed into culture in P12 plates at 37° C. for one day in MEM medium. Serial dilutions of antiviral (0.5-50 or 1-550 ìM) were added to the cells which were again incubated à 37° C. for 24 or 48 hours. At the end of kinetics, 20 ìl of the MTT reactant (3-[4,5-dimethylthiazol-2-yl]-2,5-diphenyl tetrazolium bromie, 7.5 mg/ml, Sigma) is added to the cells and incubated at 37° C. for 1 h. After rinsing the cells, 100 ìl DMSO is added to every well. The absorbance is measured at 550 nm after subtraction of the white at 650 nm using a plate reader (PerkinElmer).

b) Antiviral Effect of the Compounds

MDCK cells ($0.32 \times 10^6$ cells/well) are placed into culture in 5% $CO_2$ for 24 hours up to approximately 80% confluence in a minimal medium (MEM, Sigma) containing 0.2% $NaHCO_3$ (Sigma), amino acids MEM (Gibco), vitamin MEM (Gibco), PSG, in the absence of foetal veal serum. The cells are then infected with the A/WSN/33 virus at a multiplicity of infection MOI=$10^{-3}$ (multi cycle growth assay) and the antiviral ((5-500 ìM) or Tamiflu (25 ìM) or the medium) are added to the cells just after the infection. Certain experiments were conducted at higher MOI=5.

The viral titers of the clarified cellular supernatants are determined on violet crystal coloured plates 24, 48 and 72 hours after infection. The experiments are conducted in a triple fold and repeated at least twice.

c) Toxicity Results:

In order to reduce the solubility issues of L410, derivative compounds were selected so that the nitro moiety of L410 is replaced with a soluble carboxylate moiety (in the form of acid salt).

Said compounds selected are as follows:

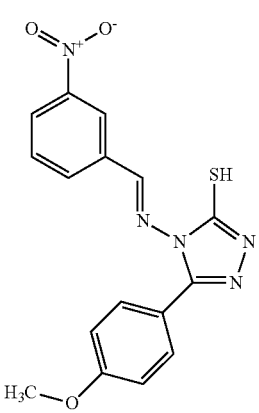

L410-Formula (H)

C72-Formula (J)

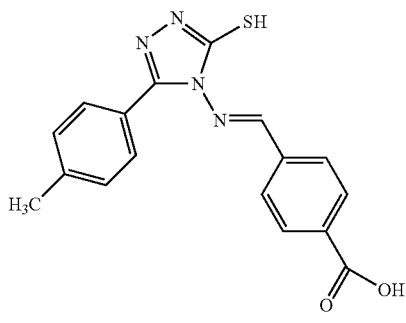

C88-Formula (K)

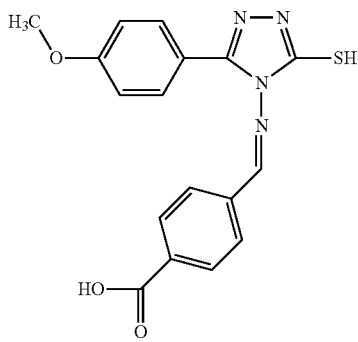

C59-Formula (I)

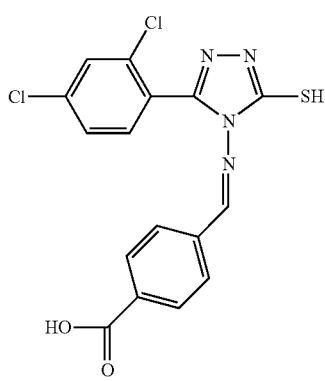

These compounds were testes on infected MDCK cells at $10^{-3}$ MOI by titering the viral titer 24 H, 48 H and 72 H after infection.

TABLE 6

Measuring the cellular toxicity of the compounds derived from triazole and of Naproxen

| Compound | Test of A549 cells | Concentration range | |
|---|---|---|---|
| Naproxen | MTT 48 H | 2-500 µM | No toxicity |
| 59 | MTT | 1-50 µM | No toxicity |
| 72 | MTT | 1-50 µM | No toxicity |
| 88 | MTT | 1-50 µM | Toxic >10 µM |
| L410 | MTT | 0.6-20 µM | No toxicity |

The results presented in table 6 show that as in the case of Naproxen, the compounds derived from triazole tested, except for the 88 compound, do not present any cellular toxicity.

TABLE 7

Test conducted on infected MDCK cells, measurements made 24 hours and 48 hours after infection of the viral titer (MOI), of the concentration of the Naproxen compounds and derivatives of triazole as well as corresponding IC10 and IC50 for each of its compounds.

| Compound | Time after infection | Viral titer Pfu/ml MDCK cells | Concentration µM | Range concentration µM | IC10 decrease × 10 viral titer/ control (n = 2) | IC50 decrease × 10 viral titer/ control (n = 2) |
|---|---|---|---|---|---|---|
| control | 24 H | $1.3 \pm 0.5 \times 10^7$ | 0 | | | |
| Naproxen | | $4.2 \pm 0.3 \times 10^5$ | 100 | 50-500 | ~50 µM | |
| 59 | | $5.5 \pm 2.5 \times 10^5$ | 50 | 5-50 | ~30 µM | ~5 µM |
| 72 | | $7.6 \pm 4.0 \times 10^5$ | 50 | 5-50 | ~20 µM | ~5 µM |
| 88 | | $1-4 \times 10^7$ | 5 | 1-5 | No effect | |
| Control | 48 H | $2.6 \pm 1.8 \times 10^8$ | 0 | | | |
| Naproxen | | $1.9 \pm 0.3 \times 10^6$ | 100 | 50-500 | ~50 µM | ~10 µM |
| L410/59 | | $2.0 \pm 0.9 \times 10^6$ | 50 | 5-50 | ~30 µM | ~3 µM |
| 72 | | $3.9 \pm 1.6 \times 10^6$ | 50 | 5-50 | ~35 µM | |
| 88 | | $1-4 \times 10^7$ | 5 | 1-5 | No effect | |

The results presented on table 7 show a decrease of the viral titer for the Naproxen compounds as well as 59 and 72 with respect to the control.

Conclusion: the compounds derived from triazole L410, 59 and 72 are antivirals approximately 2 to 4 times more efficient than Naproxen, without cellular toxicity.

The invention claimed is:

1. A method of treating an infection by a type-A Influenza virus in a mammal subject, the method comprising the administration to a subject in need thereof of a therapeutically effective quantity of a composition comprising a compound having a property of acting as an inhibitor of the fixation of viral RNA to the nucleoprotein of type-A Influenza viruses, said compound being capable of binding to a site forming a sphere of at least 12 Ångströms (Å) in diameter centered on the Tyr 148 residue, belonging to the binding domain of the viral RNA on said nucleoprotein, said domain:

comprising the amino acids Arg65, Gln149, Tyr148, Arg150, Arg152, Arg156, Arg174, Arg175, Arg195, Arg199, Arg213, Arg214, Arg221, Arg236, Pro354, Arg355, Lys357, Arg361, Arg391, Lys184, Lys198, Gly212, Ile217, Ala218, Lys227, Lys229, Lys273 and Val353 of a sequence comprising SEQ ID NO: 1, and being delineated by two loops, a first loop comprising the amino acid residues Glu73 to Lys90 and a second loop comprising the amino acid residues Gly200 to Arg214 of a sequence comprising SEQ ID NO: 1, wherein said compound is a naproxen derivative of formula (B):

Formula (B)

wherein:

$R_1$=-Ph(COOH)$_2$, or —CHR$_5$R$_6$;

$R_5$=—(CH$_2$)$_n$COOH, with n=0-2;

$R_6$=—(CH$_2$)$_n$COOH, with n=0-2;

$R_2$=H;

$R_3$=—CH$_3$; and $R_4$=H.

2. The method of claim 1, wherein the sequence comprising SEQ ID NO: 1 is SEQ ID NO: 2.

3. The method of claim 1, wherein said binding domain comprises more than 10% arginine amino acid residues.

4. The method of claim 1, wherein said subject is a human.

5. A compound having a property of acting as an inhibitor of the fixation of viral RNA to the nucleoprotein of type-A Influenza viruses, said compound capable of binding to a site forming a sphere of at least 12 Ångstroms (Å) in diameter centred on the Tyr 148 residue, belonging to the binding domain of the viral RNA on said nucleoprotein, said domain:

comprising the amino acids Arg65, Gln149, Tyr148, Arg150, Arg152, Arg156, Arg174, Arg175, Arg195, Arg199, Arg213, Arg214, Arg221, Arg236, Pro354, Arg355, Lys357, Arg361, Arg391, Lys184, Lys198, Gly212, Ile217, Ala218, Lys227, Lys229, Lys273 and Val353 of a sequence comprising SEQ ID NO: 1, and being delineated by two loops, a first loop comprising the amino acid residues Glu73 to Lys90 and a second loop comprising the amino acid residues Gly200 to Arg214 of a sequence comprising SEQ ID NO: 1, wherein said compound is a naproxen derivative of formula (B):

Formula (B)

wherein:

$R_1$=-Ph(COOH)$_2$, or —CHR$_5$R$_6$;

$R_5$=—(CH$_2$)$_n$COOH, with n=0-2;

$R_6$=—(CH$_2$)$_n$COOH, with n=0-2;

$R_2$=H;

$R_3$=—CH$_3$; and $R_4$=H.

6. The compound of claim 5, wherein said compound has the formula (F) or (G)

Formula (F)

Formula (G)

7. The method of claim 1, wherein said binding domain comprises more than 20% arginine amino acid residues.

8. The method of claim 1, wherein said compound has the formula (F) or (G)

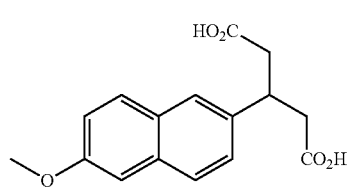
Formula (F)
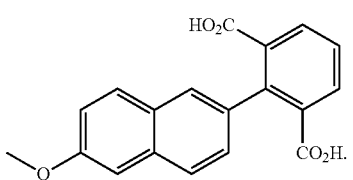
Formula (G)
9. The method of claim 5, wherein in Formula B, $R_6$ is identical to $R_5$.
* * * * *